United States Patent
Mudiyam et al.

(10) Patent No.: US 12,406,363 B2
(45) Date of Patent: Sep. 2, 2025

(54) SYSTEM AND METHOD FOR AUTOMATICALLY ESTIMATING KNEE CARTILAGE THICKNESS FOR FEMORAL, TIBIAL, PATELLAR, AND MENISCAL CARTILAGES

(71) Applicant: GE Precision Healthcare LLC, Wauwatosa, WI (US)

(72) Inventors: Veerasravanthi Mudiyam, Kurnool (IN); Deepthi Sundaran, Bangalore (IN); Jignesh Dholakia, Bangalore (IN); Maggie Fung, Jersey City, NJ (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 381 days.

(21) Appl. No.: 18/118,250

(22) Filed: Mar. 7, 2023

(65) Prior Publication Data
US 2024/0303805 A1 Sep. 12, 2024

(51) Int. Cl.
*G06T 7/00* (2017.01)
*A61B 5/00* (2006.01)

(52) U.S. Cl.
CPC .......... *G06T 7/0012* (2013.01); *A61B 5/4514* (2013.01); *G06T 2207/30008* (2013.01)

(58) Field of Classification Search
CPC ......... G06T 7/0012; G06T 2207/30008; G06T 7/62; G06T 7/11; G06T 7/136; G06T 7/60; G06T 2207/10024; G06T 2207/10088; G06T 2207/20104; G06T 2207/30012; A61B 5/4514; A61B 5/055
See application file for complete search history.

(56) References Cited

U.S. PATENT DOCUMENTS 12,211,151 B1 * 1/2025 Chiou .................. G06T 19/003
2017/0258526 A1 * 9/2017 Lang .................. A61B 17/1742

FOREIGN PATENT DOCUMENTS

AU    2012296556 A1 * 3/2014 ........... A61B 17/155

OTHER PUBLICATIONS

Koo et al., "Morphology And Thickness In Tibial And Femoral Cartilage At The Knee Is Influenced By The Mechanics Of Walking," 2003 Summer Bioengineering Conference, Jun. 25-29, Sonesta Beach Resort in Key Biscayne, Florida, 2 pgs.

(Continued)

*Primary Examiner* — Darryl V Dottin
(74) *Attorney, Agent, or Firm* — Fletcher Yoder, P.C.

(57) ABSTRACT

A computer-implemented method for estimating cartilage includes pre-processing, via a processor, a segmented image of region of interests (ROIs) of a subject to separate the ROIs into individual ROI volumes, wherein the ROI volumes comprise at least one cartilage region. The computer-implemented method also includes performing, via the processor, surface separation between a respective subchondral surface and a respective articular surface for each ROI volume to extract a respective separate subchondral surface and a respective separate articular surface for each ROI volume. The computer-implemented method further includes estimating, via the processor, cartilage statistics for the at least one cartilage region utilizing a nearest neighbor algorithm based on the respective separate subchondral surface and the respective separate articular surface for each ROI volume.

21 Claims, 21 Drawing Sheets

(56) References Cited

OTHER PUBLICATIONS

Mackay et al., "Three-Dimensional Surface-Based Analysis of Cartilage MRI Data in Knee Osteoarthritis: Validation and Initial Clinical Application," Journal of Magnetic Resonance Imaging, International Society for Magnetic Resonance in Medicine, 2020, 13 pgs, Wiley Periodicals LLC.
Stammberger et al., "Determination of 3D Cartilage Thickness Data From MR Imaging: Computational Method and Reproducibility in the Living," Magnetic Resonance in Medicine, vol. 41, 1999, 8 pgs, Wiley Online Library.
Schmitz et al., "Evaluation of knee cartilage thickness: A comparison between ultrasound and magnetic resonance imaging methods," 2016, Elsevier B.V., 7 pgs.
Carballido-Gamio et al., "Inter-subject comparison of MRI knee cartilage thickness," 2007, Elsevier B.V., 16 pgs.
Norman et al., "Use of 2D U-Net Convolutional Neural Networks for Automated Cartilage and Meniscus Segmentation of Knee MR Imaging Data to Determine Relaxometry and Morphometry," radiology.rsna.org n Radiology: vol. 288: No. 1—Jul. 2018, 9 pgs.
Oshinsky et al., "3D Visualization of Cartilage Thickness in Knee Joint Using Bezier Spline Segmentation," Proc. Intl. Soc. Mag. Reson. Med., 11, 2003, 1 pg.
Maier et al., "Comparison of Different Approaches for Measuring Tibial Cartilage Thickness," Journal of Integrative Bioinformatics. 2017; 10 pgs.
Bonaretti et al., "pyKNEEr: An image analysis workflow for open and reproducible research on femoral knee cartilage," Plos One, Jan. 24, 2020, 19 pgs, https://doi.org/10.1371/journal.pone.0226501.
Solloway et al., "The Use of Active Shape Models for Making Thickness Measurements of Articular Cartilage from MR Images," 1997, Wiley Online Library, 10 pgs.
Si et al., "Knee Cartilage Thickness Differs Alongside Ages: A 3-T Magnetic Resonance Research Upon 2,481 Subjects via Deep Learning," Frontiers in Medicine, Feb. 2021, vol. 7, Article 600049, 10 pgs.
Fiorentino et al., "A deep-learning framework for metacarpal-head cartilage-thickness estimation in ultrasound rheumatological images," Computers in Biology and Medicine, 2021, Elsevier Ltd., 10 pgs, https://doi.org/10.1016/j.compbiomed.2021.105117.
Panfilov et al., "Deep learning-based segmentation of knee MRI for fully automatic subregional morphological assessment of cartilage tissues: Data from the Osteoarthritis Initiative," Journal of Orthopaedic Research, 2021, 12 pgs.
Nolte et al., "Getting Cartilage Thickness Measurements Right: A Systematic Inter-Method Comparison Using MRI Data from the Osteoarthritis Initiative," 2023, Sage Publications, 13 pgs.

* cited by examiner

364

| Femur | RAS co-ordinates | Thickness Measured by Clinical Experts(mm) | Thickness Measured from Algorithm(mm) | Error(mm) |
|---|---|---|---|---|
| | R96.0 A77.1 S36.6 R95.9 A78.2 S36.0 | 1.257 | 1.4425 | 0.1855 |
| | R98.7 A57.8 S18.7 R98.7 A58.3 S17.1 | 1.676 | 1.3 | 0.376 |
| | R104.5 A16.4 S35.4 R104.8 A14.1 S35.2 | 2.328 | 2.1325 | 0.1955 |
| Average(mm) | | 1.736 | 1.625 | 0.252 |

366

| Femur | RAS co-ordinates | Thickness Measured by Clinical Experts(mm) | Thickness Measured from Algorithm(mm) | Error(mm) |
|---|---|---|---|---|
| | R88.0 A80.2 S3.8 R88.2 A81.7 S2.3 | 2.131 | 2.4123 | 0.2813 |
| | R85.1 A52.8 I12.6 R85.1 A52.9 I13.9 | 1.3038 | 1.252 | 0.0518 |
| | R80.8 A17.1 S3.9 R80.5 A14.8 S3.4 | 2.372 | 2.052 | 0.32 |
| Average(mm) | | 1.935 | 1.9 | 0.2177 |

368

| Femur | RAS co-ordinates | Thickness Measured by Clinical Experts(mm) | Thickness Measured from Algorithm(mm) | Error(mm) |
|---|---|---|---|---|
| | R63.1 A63.7 S17.0 R63.1 A64.9 S15.7 | 1.769 | 1.8125 | 0.0435 |
| | R63.5 A39.6 S4.3 R63.5 A39.6 S3.3 | 1.0 | 0.9425 | 0.0575 |
| | R63.9 A11.8 S21.5 R63.9 A10.1 S21.1 | 1.746 | 1.4825 | 0.2635 |
| Average(mm) | | 1.505 | 1.4125 | 0.1214 |

| Tibia | RAS co-ordinates | Thickness Measured by Clinical Experts(mm) | Thickness Measured from Algorithm(mm) | Error(mm) |
|---|---|---|---|---|
| | R100.2 A47.7 S10.2<br>R100.1 A48.3 S11.5 | 1.435 | 1.44 | 0.005 |
| | R102.0 A34.5 S10.1<br>R102.1 A34.0 S14.3 | 4.23 | 3.88 | 0.35 |
| | R103.7 A22.7 S8.5<br>R103.7 A22.0 S9.9 | 1.565 | 1.44 | 0.125 |
| Average(mm) | | 2.41 | 2.25 | 0.16 |

372

| Tibia | RAS co-ordinates | Thickness Measured by Clinical Experts(mm) | Thickness Measured from Algorithm(mm) | Error(mm) |
|---|---|---|---|---|
| | R80.7 A56.8 I17.3<br>R80.6 A56.6 I14.5 | 2.809 | 2.98 | 0.171 |
| | R79.7 A48.7 I17.8<br>R79.7 A48.8 I15.9 | 1.902 | 2.02 | 0.118 |
| | R78.0 A33.5 I19.2<br>R77.9 A32.7 I17.2 | 2.15 | 2.14 | 0.1 |
| Average(mm) | | 2.287 | 2.38 | 0.13 |

374

| Tibia | RAS co-ordinates | Thickness Measured by Clinical Experts(mm) | Thickness Measured from Algorithm(mm) | Error(mm) |
|---|---|---|---|---|
| | R63.4 A46.4 S3.3<br>R63.4 A46.5 S3.9 | 1.608276 | 0.4 | 0.208 |
| | R63.7 A31.0 S1.9<br>R63.7 A31.2 S3.9 | 2.01 | 1.64 | 0.37 |
| | R63.9 A17.0 S3.2<br>R63.9 A17.0 S4.0 | 0.799 | 0.74 | 0.059 |
| Average(mm) | | 1.139 | 0.9266 | 0.212 |

| Patella | RAS co-ordinates | Thickness Measured by Clinical Experts(mm) | Thickness Measured from Algorithm(mm) | Error(mm) |
|---|---|---|---|---|
| | R94.9 A85.0 S50.9 R95.1 A83.3 S51.4 | 1.783 | 2.00 | 0.217 |
| | R95.1 A83.5 S44.3 R95.4 A81.6 S44.9 | 2.015 | 1.88 | 0.135 |
| | R95.4 A81.3 S37.9 R95.6 A80.1 S38.3 | 1.28 | 1.48 | 0.2 |
| Average(mm) | | 1.693 | 1.786 | 0.184 |

378

| Patella | RAS co-ordinates | Thickness Measured by Clinical Experts(mm) | Thickness Measured from Algorithm(mm) | Error(mm) |
|---|---|---|---|---|
| | R88.8 A90.3 S36.6 R88.6 A88.4 S36.5 | 1.913 | 2.19 | 0.277 |
| | R88.9 A90.0 S26.3 R88.5 A86.6 S26.7 | 3.44 | 3.53 | 0.09 |
| | R88.8 A88.8 S17.5 R88.6 A87.1 S17.5 | 1.711 | 1.85 | 0.139 |
| Average(mm) | | 2.355 | 2.523 | 0.168 |

380

| Patella | RAS co-ordinates | Thickness Measured by Clinical Experts(mm) | Thickness Measured from Algorithm(mm) | Error(mm) |
|---|---|---|---|---|
| | R62.9 A78.0 S38.2 R62.9 A75.0 S39.6 | 3.31 | 2.11 | 1.2 |
| | R62.9 A75.8 S31.7 R63.0 A72.5 S33.5 | 3.76 | 2.70 | 1.06 |
| | R63.0 A71.1 S23.4 R63.0 A69.2 S24.2 | 2.06 | 1.75 | 0.31 |
| Average(mm) | | 3.043 | 2.186 | 0.856 |

FIG. 22

SYSTEM AND METHOD FOR AUTOMATICALLY ESTIMATING KNEE CARTILAGE THICKNESS FOR FEMORAL, TIBIAL, PATELLAR, AND MENISCAL CARTILAGES

BACKGROUND

The subject matter disclosed herein relates to medical imaging and, more particularly, to a system and a method for automatically estimating knee cartilage thickness for femoral, tibial, patellar, and meniscal cartilages.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MRI, when a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

Osteoarthritis (OA) is a serious, painful, degenerative joint disease that affects a large population, and the increasing trend of teenagers having OA has been an alarming issue in recent years. Though arthritis is more common in older people, sports injuries can raise the risk of early onset of arthritis. This means that arthritis develops at a younger age than what doctors consider normal. Examples of sports-related injuries include torn cartilage or ligaments and broken bones. Osteoarthritis can affect the joints of the spine, fingers, thumbs, hips, knees, and toes, but it is most common in the knee. This degenerative joint disease leads to a progressive and irreversible loss of cartilage with consequent pain, stiffness, and limitation of daily activities. One of the ways in which clinicians assess the health of these cartilages is by estimating their thickness from the bone they are covering and supporting, and MRI plays a vital role in imaging these cartilages for assessment. A visual assessment made by the clinician on MR images does not guarantee accurate investigation, hence a quantitative analysis of these scanned images is needed to get accurate thicknesses of the cartilages for clinicians to proceed with the treatment. In addition, visual assessment is time consuming and prolonged visual inspection can invariably result in fatigue for the radiologist. Further, manually estimating the thicknesses of the cartilages is inherently more error-prone and is vulnerable to inter-person and intra-person variability in the estimates.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for estimating cartilage thickness is provided. The computer-implemented method includes pre-processing, via a processor, a segmented image of region of interests (ROIs) of a subject to separate the ROIs into individual ROI volumes, wherein the ROI volumes comprise at least one cartilage region. The computer-implemented method also includes performing, via the processor, surface separation between a respective subchondral surface and a respective articular surface for each ROI volume to extract a respective separate subchondral surface and a respective separate articular surface for each ROI volume. The computer-implemented method further includes estimating, via the processor, cartilage statistics for the at least one cartilage region utilizing a nearest neighbor algorithm based on the respective separate subchondral surface and the respective separate articular surface for each ROI volume.

In another embodiment, a system for estimating knee cartilage thickness is provided. The system includes a memory encoding processor-executable routines. The system also includes a processor configured to access the memory and to execute the processor-executable routines, wherein the routines, when executed by the processor, cause the processor to perform actions. The actions include pre-processing a segmented image of region of interests (ROIs) of a knee of a subject to separate the ROIs into individual ROI volumes, wherein the ROI volumes comprise at least one cartilage region. The actions also include performing surface separation between a respective subchondral surface and a respective articular surface for each ROI volume to extract a respective separate subchondral surface and a respective separate articular surface for each ROI volume. The actions further include estimating cartilage thickness values for the at least one cartilage region utilizing a nearest neighbor algorithm based on the respective separate subchondral surface and the respective separate articular surface for each ROI volume.

In a further embodiment, a non-transitory computer-readable medium, the computer-readable medium including processor-executable code that when executed by a processor, causes the processor to perform actions. The actions include pre-processing a 5-class segmented image of region of interests (ROIs) of a knee of a subject to separate the ROIs into individual ROI volumes, wherein the ROI volumes comprise at least one cartilage region. The actions also include performing surface separation between a respective subchondral surface and a respective articular surface for each ROI volume to extract a respective separate subchondral surface and a respective separate articular surface for each ROI volume. The actions further include estimating cartilage thickness values for the at least one cartilage region utilizing a nearest neighbor algorithm based on the respective separate subchondral surface and the respective separate articular surface for each ROI volume, wherein pre-processing the segmented image, performing surface separation, and estimating cartilage thickness values all occur without utilizing deep-learning

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 20 depicts tables of results of manual validation of femoral cartilage thickness;

FIG. 21 depicts tables of results of manual validation of tibial cartilage thickness; and FIG. 22 depicts tables of results of manual validation of patellar cartilage thickness.

DETAILED DESCRIPTION

Figure 1:
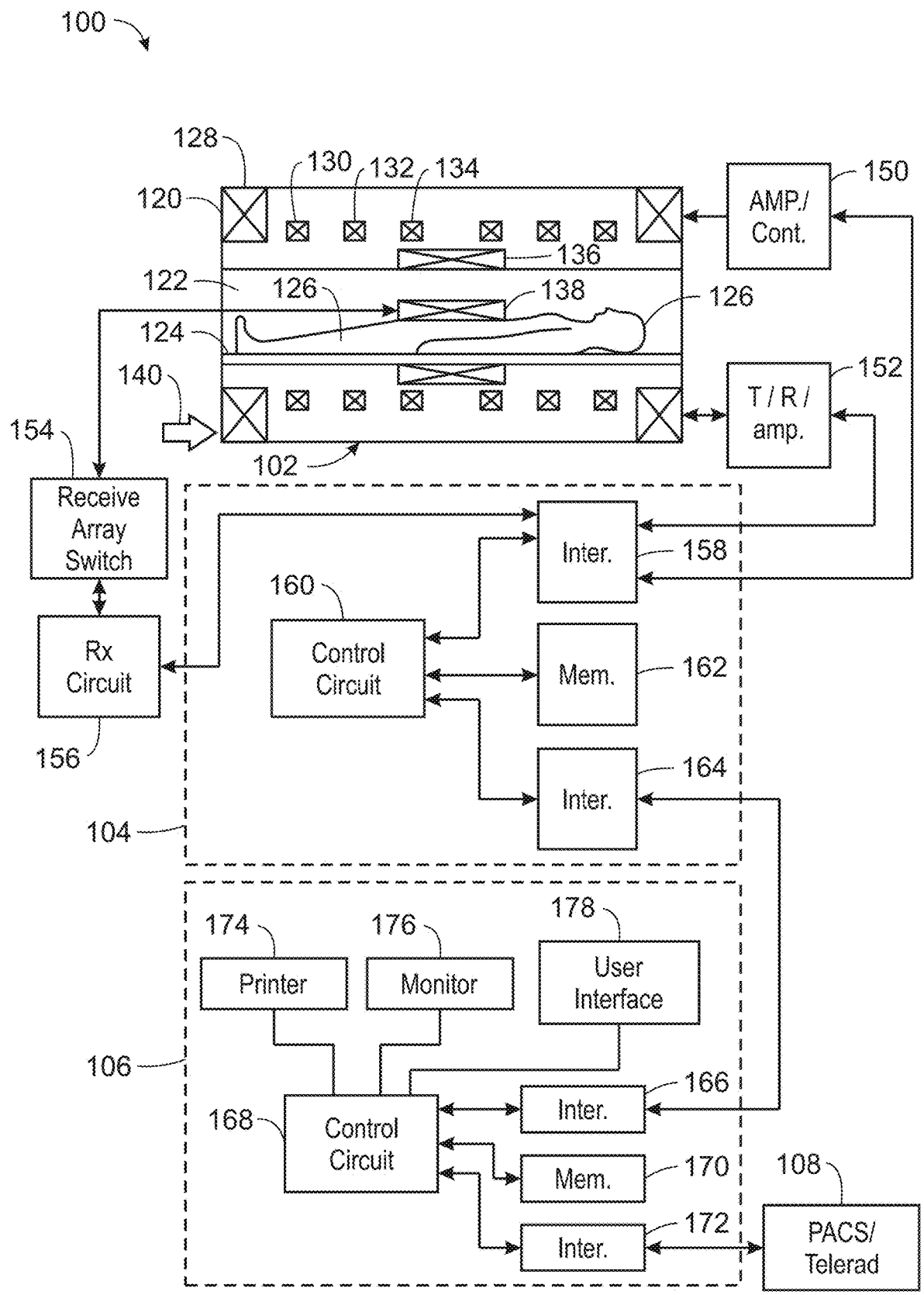
FIG. 1 illustrates an embodiment of a magnetic resonance imaging (MRI) system suitable for use with the disclosed technique.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

In the following disclosure, subchondral surface/bone surface refers to a cartilage surface that is adjacent to the bone that it is attached to. Articular surface/cartilage surface means the cartilage surface that is located away from the bone it attached to.

There are three important bones that come together at the knee joint: the femur (thigh bone), the tibia (shin bone) and the patella (kneecap) The femur, tibia and patella are covered with a smooth layer of cartilage where they contact each other at the knee joint. The other type of cartilage in the knee joint is called the meniscus. The meniscus is a shock absorber that sits between the end of the femur and the top of the tibia.

The present disclosure provides systems and methods for automatically estimating knee cartilage thickness for femoral, tibial, patellar, and meniscal cartilages. In particular, the present disclosure provides an easy, generic and less computationally intensive algorithm that can be used to estimate the thickness of all 4 cartilages (femoral, tibial, patellar, and meniscal) which can be visualized in two-dimensional (2D) (flatten view) or three-dimensional (3D) view. On the acquired MRI knee images 5-class segmentation is performed, using deep learning to separate the images into different region of interests (ROIs) such as femoral, tibial region, patellar region, meniscal region, and background. In certain embodiments, conventional image processing methods may be utilized for segmentation or segmentation may be done manually by a clinical expert. The thickness algorithm involves separating the bone surface from cartilage surface in each of the four cartilages using a series of chosen morphological processes and then utilizing a nearest neighbor algorithm to calculate the thickness. The thickness values are then encoded onto one of the surfaces (usually the surface closer to the bone) and projected to the appropriate image plane to visualize the same in 2D. The thickness encoded volumes are also converted to digital imaging and communications in medicine (DICOM) files to facilitate 3D visualization in DICOM viewers. It should be noted that the techniques disclosed herein may be applied to other anatomical regions (e.g., hip).

The disclosed embodiments enable accurate analysis of cartilage thickness values over time to help in assessing progression of cartilage degeneration (if any) and early treatment. In addition, the disclosed embodiments provide an automated technique for estimating cartilage thickness that avoids the drawbacks of other techniques while also enabling a faster diagnosis. Further, the disclosed embodiments do not utilize deep learning techniques in estimating the cartilage thickness values, thus, reducing computing and/or processing requirements on the system and delivering faster throughput. Even further, the disclosed embodiments provide a standardized way for computing the estimates that ensure high repeatability and improved measurement accuracy over time. Still further, as the estimated cartilage thickness values are quantitative, the disclosed embodiments provide a better assessment of progression of degeneration over time. Yet further, the disclosed embodiments provide for different techniques for the user to visualize and report the findings from thickness maps which may further aid in diagnosis and treatment.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, $B_0$. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, the memory circuit 170 may store one or more neural networks for reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
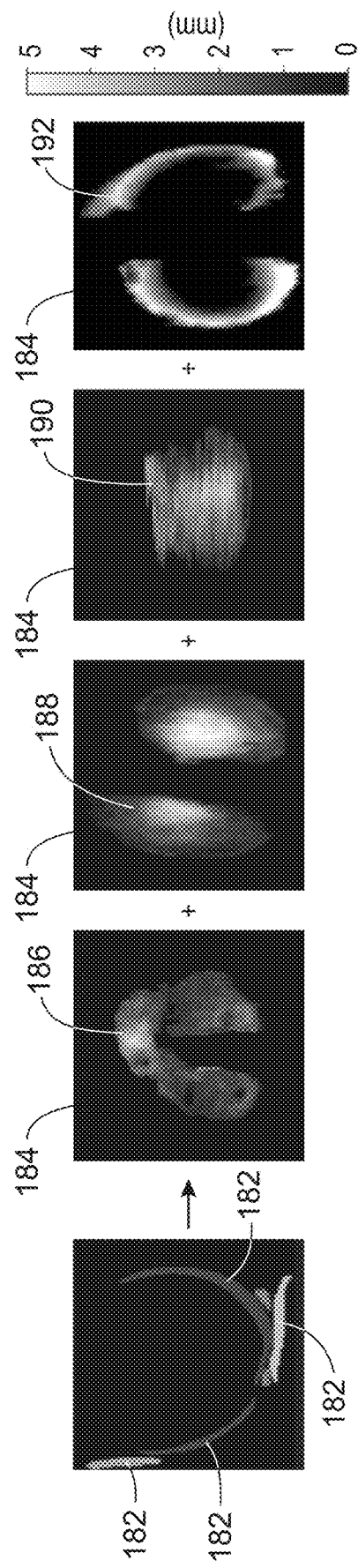
FIG. 2 illustrates a schematic diagram of the outcome of utilizing an algorithm to generate cartilage thickness heat maps, in accordance with aspects of the present disclosure.

FIG. 2 illustrates a schematic diagram of the outcome of utilizing an algorithm (e.g., thickness estimation algorithm) to generate cartilage thickness heat maps. As depicted, an algorithm (e.g. without utilizing deep learning techniques) receives a 5-class segmented image 180 of region of interests (ROIs) 182 of a knee of a subject (e.g., patient). The 5-class segmented image 180 is derived from segmentation (e.g., 5-class segmentation) of an image (e.g., MR image) acquired utilizing MRI scanner (e.g., MRI scanner 102 of the MRI system in FIG. 1). Each segmented ROI 182 is labelled. Along with the background, the ROIs 182 include a femoral cartilage region, a tibial cartilage region, a patellar cartilage region, and a meniscal cartilage region. The knee MRI image may be acquired utilizing a sagittal isotropic 3D fast (turbo) spin echo sequence optimized for half Fourier parallel imaging, with long echo trains, low flip angles, and low specific absorption rates or another sequence for knee imaging. In certain embodiments, the methods described herein may be applied to non-sagittal knee acquisitions (after applying suitable reformatting techniques as needed. The knee MRI image may be segmented utilizing a deep learning-based technique or using conventional image processing methods or manually by a clinical expert. As depicted, the algorithm outputs heat maps 184 for the visualization of the knee cartilage thickness values for the different cartilage regions of the knee. As depicted in FIG. 2, the heat maps 184 include a femoral cartilage heat map 186, tibial cartilage heat map 188, a patellar cartilage map 190, and a meniscal cartilage heat map 192.

Figure 3:
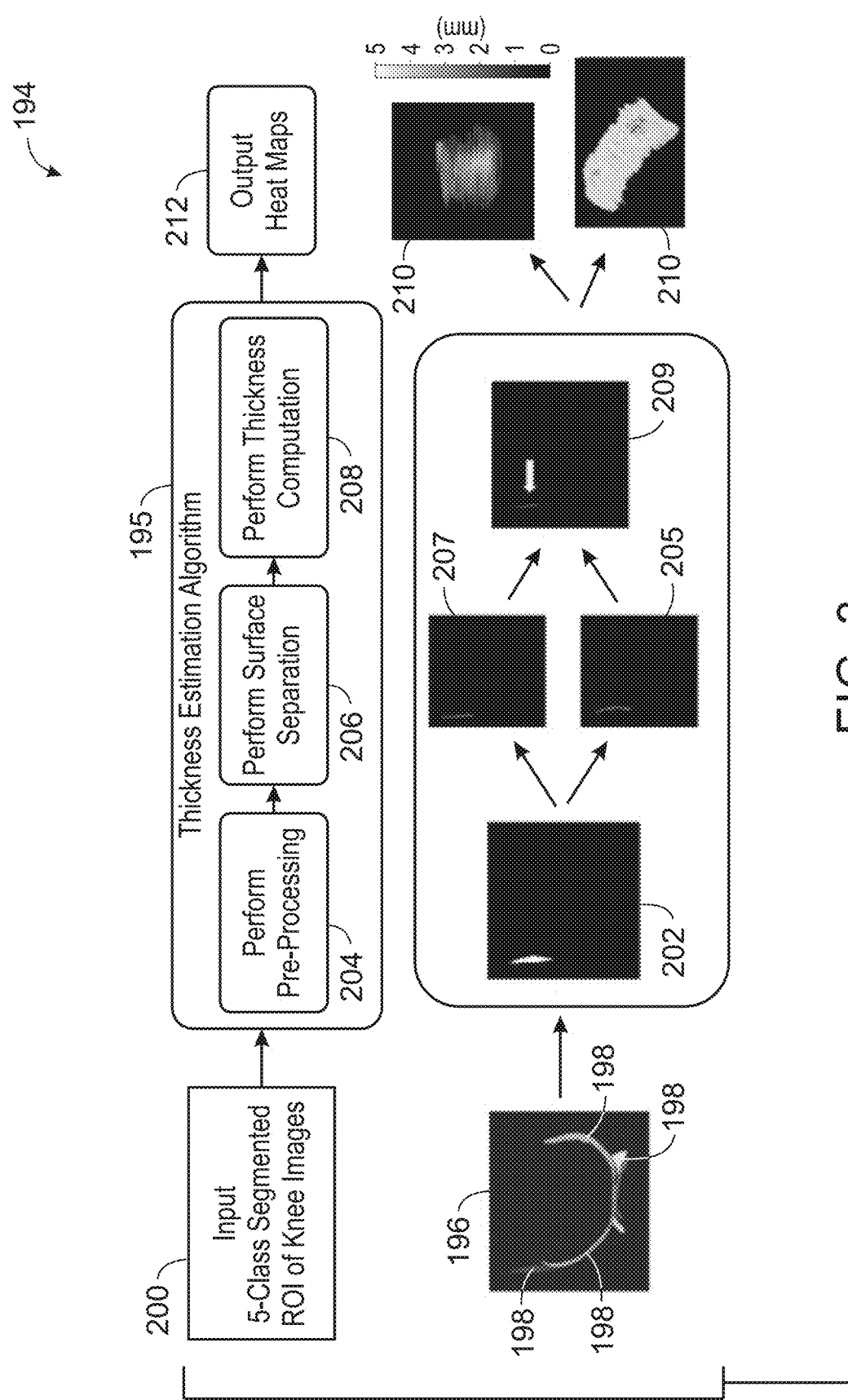
FIG. 3 illustrates a schematic diagram of a method for estimating knee cartilage thickness, in accordance with aspects of the present disclosure.

FIG. 3 illustrates a schematic diagram of a method 194 for estimating knee cartilage thickness for each of the knee cartilages: femoral cartilage, tibial cartilage, patellar cartilage, and meniscal cartilage. One or more steps of the method 194 may be performed by processing circuitry of the magnetic resonance imaging system 100 in FIG. 1 or a remote computing system. The method 194 may be utilized on multiple slices of MRI image data.

The method 194 includes inputting into an algorithm 195 (e.g., thickness estimation algorithm) a 5-class segmented image 196 of region of interests (ROIs) 198 of a knee of a subject (e.g., patient) (block 200). The 5-class segmented image 196 is derived from segmentation (e.g., 5-class segmentation) of an image (e.g., MR image) acquired utilizing MRI scanner (e.g., MRI scanner 102 of the MRI system in FIG. 1). Each segmented ROI 198 is labelled. Along with the background, the ROIs 198 include a femoral cartilage region, a tibial cartilage region, a patellar cartilage region, and a meniscal cartilage region.

In determining the cartilage thickness for each of the knee cartilages, the algorithm 195 performs three steps. In addition, the algorithm 195 does not utilize deep-learning based techniques to determine cartilage thickness. For the first step performed by the algorithm 195, the method 194 includes pre-processing the 5-class segmented image 196 to separate the ROIs 198 into individual ROI volumes 202 (block 204). The ROI volumes 202 include a femoral cartilage region or volume, a tibial cartilage region or volume, a patellar cartilage region or volume, and a meniscal cartilage region or volume.

For the second step performed the algorithm 195, the method 194 includes performing surface separation between a respective subchondral surface and a respective articular surface for each ROI volume 202 to extract a respective separate subchondral surface (e.g., subchondral surface volume) 205 and a respective separate articular surface (e.g., articular surface volume) 207 for each ROI volume 202 (block 206). In particular, a respective separate subchondral surface 205 and a respective separate articular surface 207 is extracted for the femoral cartilage region or volume, the tibial cartilage region or volume, the patellar cartilage region or volume, and the meniscal cartilage region or volume.

For the third step of the algorithm 195, the method 194 includes estimating respective cartilage thickness values for each of femoral cartilage, tibial cartilage, patellar cartilage, and meniscal cartilage utilizing a nearest neighbor algorithm based on the respective separate subchondral surface 205 and the respective separate articular surface 207 for each ROI volume 202 and generating a respective thickness volume 209 for each of the femoral cartilage, the tibial cartilage, the patellar cartilage, and the meniscal cartilage with the respective cartilage thickness values encoded to pixels of either the respective separate subchondral surface 205 or the respective separate articular surface 207 (block 208). As depicted in FIG. 3, the thickness volume 209 is obtained from the pixels of the separate subchondral surface 205.

The method 194 includes outputting heat maps 210 (based on the thickness volumes 209) for the visualization of the knee cartilage thickness values for the different cartilage regions of the knee (block 212). As depicted in FIG. 2, the heat maps 184 include a femoral cartilage heat map 186, a tibial cartilage heat map 188, a patellar cartilage map 190, and a meniscal cartilage heat map 192. In certain embodiments, the visualization of the knee cartilage thickness values for the different cartilage regions of the knees may in the form of two-dimensional or three dimensional color maps or surface/volume renderings. In certain embodiments, these two-dimensional or three dimensional color maps or surface/volume renderings may be exported or saved in a three-dimensional printer compatible format for utilization with a three-dimensional printer.

Figure 4:
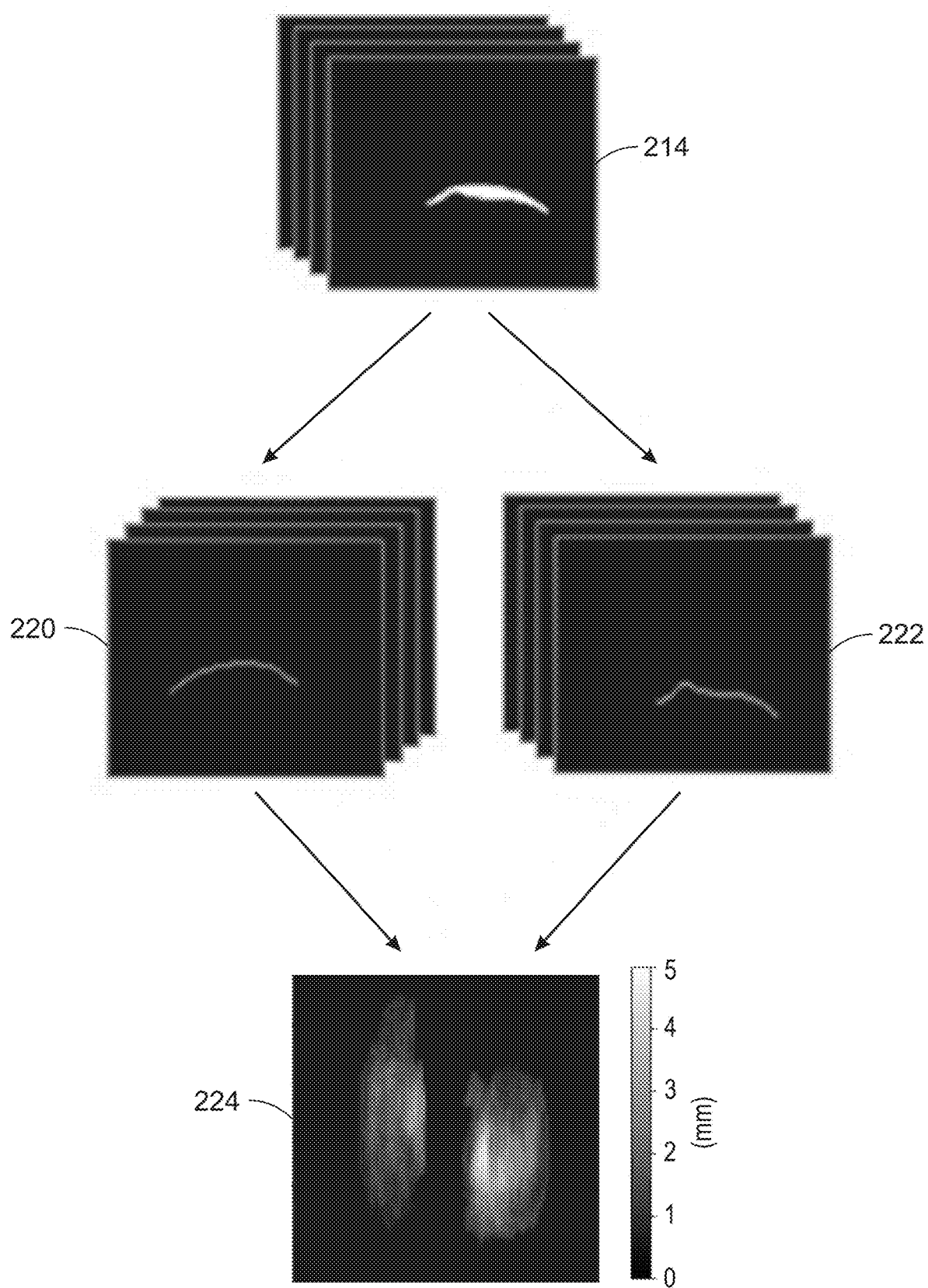
FIG. 4 illustrates a schematic diagram of the process for estimating knee cartilage thickness for tibial cartilage, in accordance with aspects of the present disclosure.

FIG. 4 illustrates a schematic diagram of the process for estimating knee cartilage thickness for tibial cartilage (e.g., utilizing the algorithm 195 in FIG. 3). FIG. 4 depicts the ROI volume 214 for the tibial cartilage region or volume 218. FIG. 4 also depicts the separated surfaces (e.g., articular surface 220 and subchondral surface 222) extracted from the tibial cartilage region. FIG. 4 further depicts a heat map 224 generated for the tibial cartilage providing a visualization of cartilage thickness values for the tibial cartilage.

Figure 5:
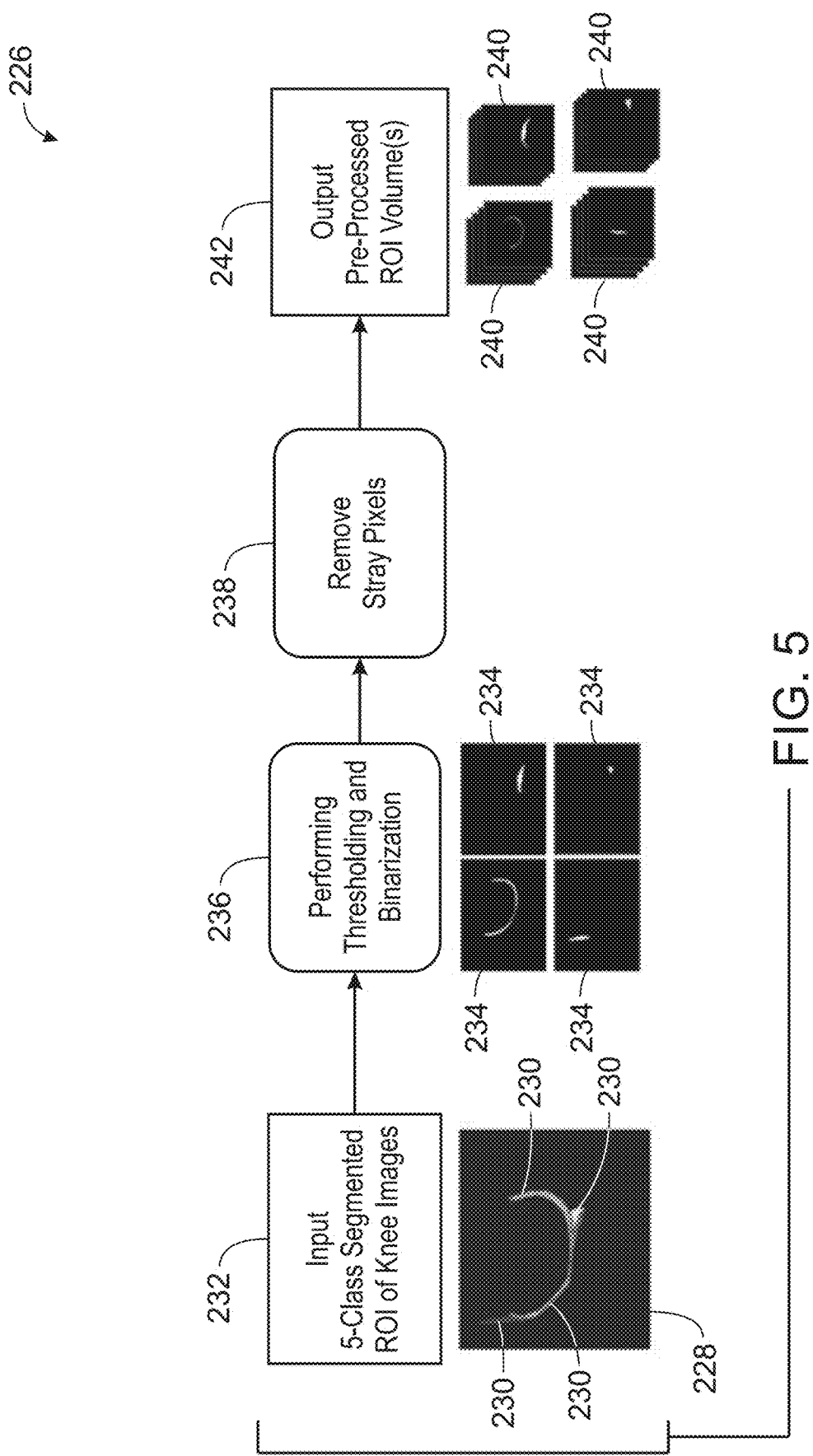
FIG. 5 illustrates a schematic diagram of a method for a pre-processing stage of a thickness estimation algorithm, in accordance with aspects of the present disclosure.

FIG. 5 illustrates a schematic diagram of a method 226 for a pre-processing stage of the thickness estimation algorithm 195 in FIG. 3. One or more steps of the method 226 may be performed by processing circuitry of the magnetic resonance imaging system 100 in FIG. 1 or a remote computing system. The method 226 may be utilized on multiple slices of MRI image data.

The method 226 includes inputting into the algorithm 195 a 5-class segmented image 228 of region of interests (ROIs) 230 of a knee of a subject (e.g., patient) (block 232). As mentioned above, the 5-class segmented image 228 is derived from segmentation (e.g., 5-class segmentation) of an image (e.g., MR image) acquired utilizing MRI scanner (e.g., MRI scanner 102 of the MRI system in FIG. 1). Each segmented ROI 230 is labelled. Along with the background, the ROIs 230 include a femoral cartilage region, a tibial cartilage region, a patellar cartilage region, and a meniscal cartilage region.

The method 226 also includes performing thresholding and binarization to extract individual ROI volumes 234 from the 5-class segmented image 228 (block 236). The individual ROI volumes 234 include a femoral cartilage volume, a tibial cartilage volume, a patellar cartilage volume, and a meniscal cartilage volume.

The method 226 further includes removing stray pixels (or voxels) from the individual ROI volumes 234 (block 238). The method 226 further includes outputting pre-processed individual ROI volumes 240 for surface separation (block 242).

Figure 6:
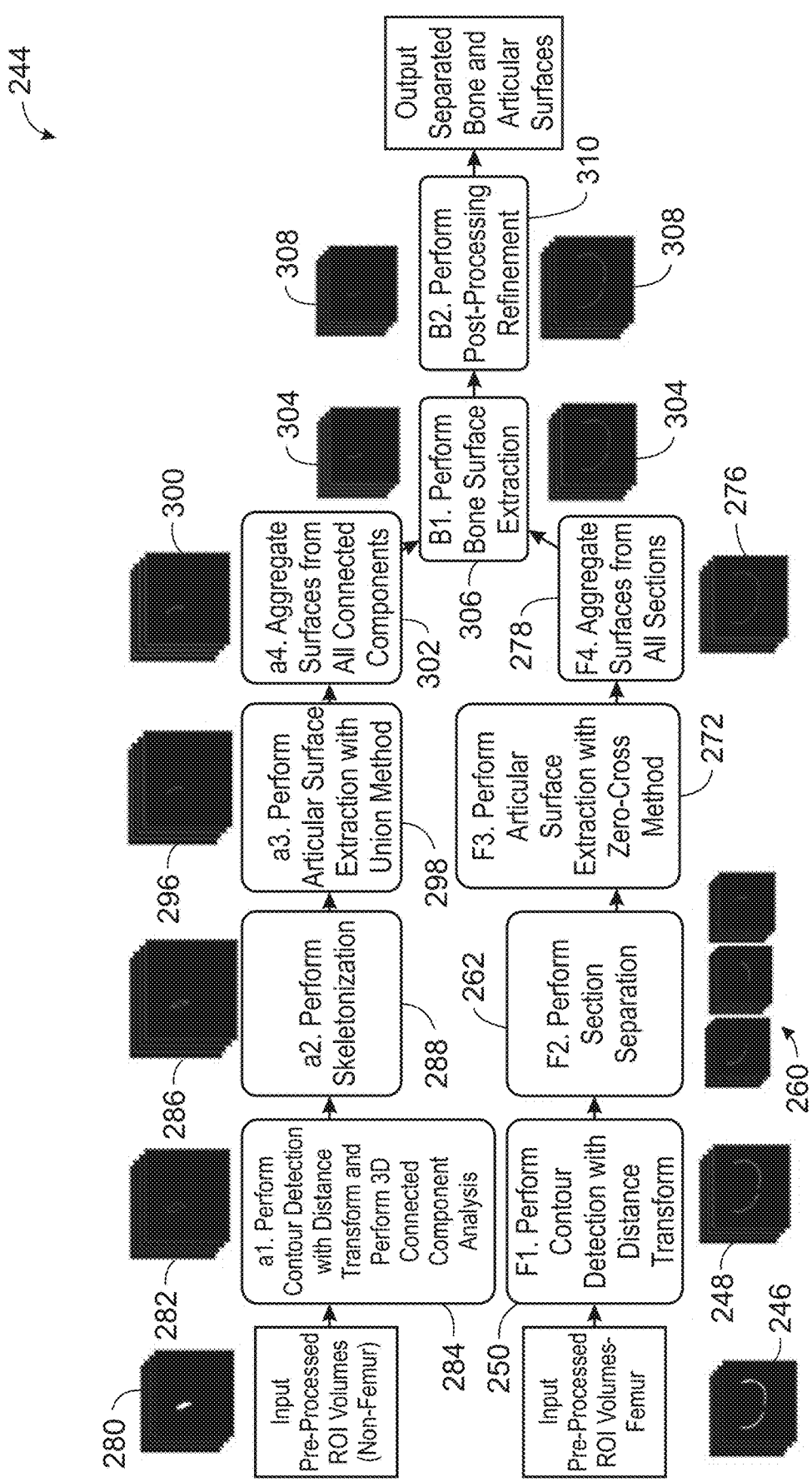
FIG. 6 illustrates a schematic diagram of a method for a surface separation stage of a thickness estimation algorithm, in accordance with aspects of the present disclosure.

FIG. 6 illustrates a schematic diagram of a method 244 for a surface separation stage of the thickness estimation algorithm 195 in FIG. 3. One or more steps of the method 244 may be performed by processing circuitry of the magnetic resonance imaging system 100 in FIG. 1 or a remote computing system. The method 244 may be utilized on multiple slices of MRI image data.

The surface separation stage is the most crucial step of the algorithm 195, where the subchondral and articular surfaces of each of the individual ROI volumes are extracted for utilization in thickness computation. The surface separation stage uses a series of image processing operations on the pre-processed cartilage volumes to separate the two surfaces of interest. Though the major steps in the process are common to all four cartilages, some of the intermediate steps are different for femoral cartilage and the other three cartilages. This is mainly due to the structural differences such as curvature and larger volume of femoral cartilage in comparison to the other cartilages that warrant additional processing to make it compatible with the algorithm 195. Steps F1, F2, F3, and F4 in the method 244 are specific to the femoral cartilage region. Steps a1, a2, a3, and a4 in the method 244 are specific to the tibial cartilage region, the patellar cartilage region, and the meniscal cartilage region. Steps B1 and B2 in the method 244 are common to the femoral cartilage region, the tibial cartilage region, the patellar cartilage region, and the meniscal cartilage region.

Figure 7:
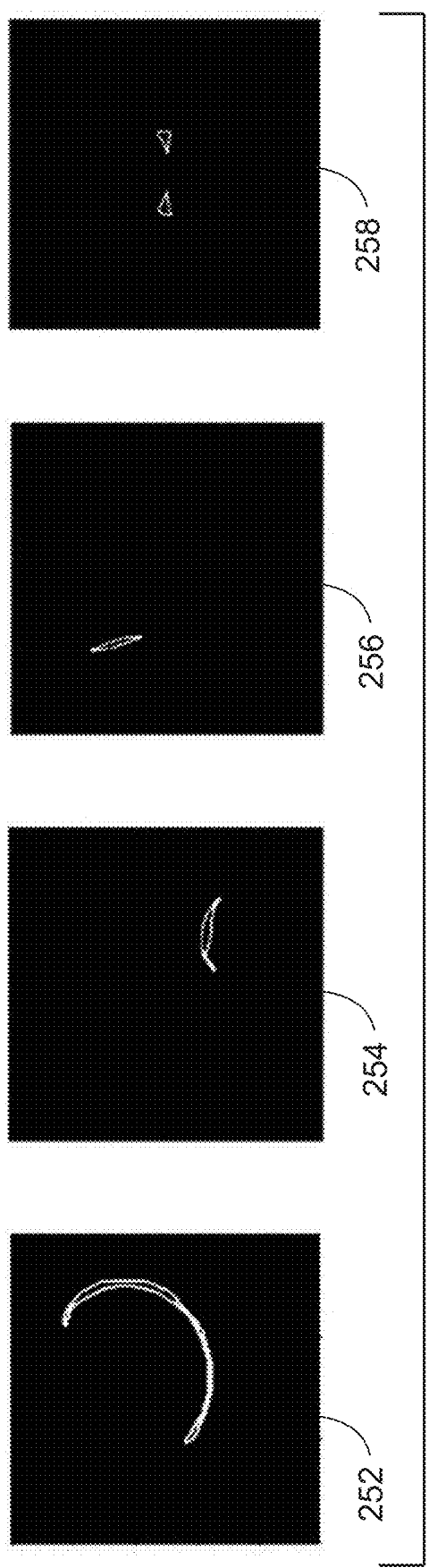
FIG. 7 depicts distance transform-based contour images for a femoral cartilage region, a tibial cartilage region, a patellar cartilage region, and a meniscal cartilage region, in accordance with aspects of the present disclosure.

For the surface separation stage for the femoral cartilage region, the method 244 includes detecting boundaries of an inputted femoral cartilage region 246 (e.g., pre-processed femoral cartilage ROI volume) utilizing distance transform to generate a contour image 248 (block 250, step F1). The distance transform method detects the inner contour of the femoral cartilage ROI volume. The result of the transform is a grayscale image that looks similar to the inputted image, except the gray level intensities of points inside the foreground regions are changed to show the distance to the closest boundary from each point. The contour of the binary image can be obtained by considering the smallest distance from the background. FIG. 7 illustrates the distance transform-based contour images 252, 254, 256, and 258 for the femoral cartilage region, the tibial cartilage region, the patellar cartilage region, and the meniscal cartilage region, respectively.

Figure 8:
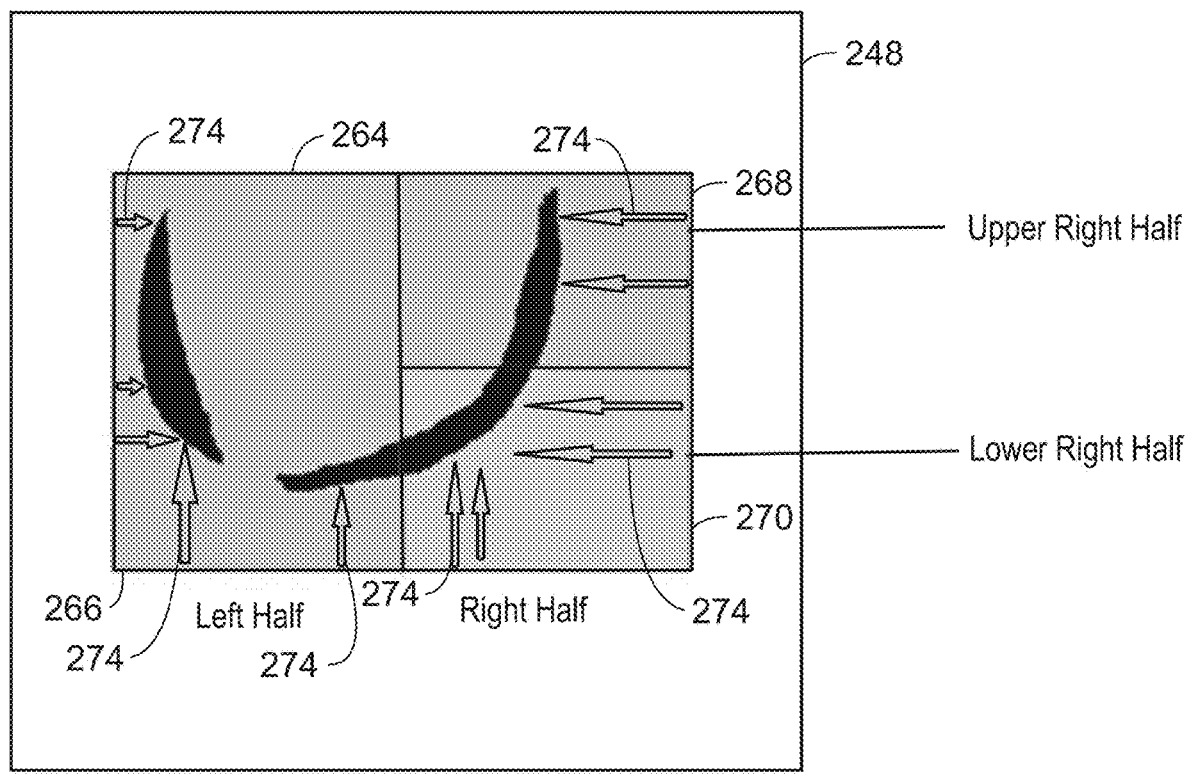
FIG. 8 illustrates section separation for a femoral cartilage region of interest, in accordance with aspects of the present disclosure.

For the surface separation stage for the femoral cartilage region, the method 244 also includes designating a bounding box for a total volume in the contour image 248 and separating the bounding box into multiple sections 260 (block 262, step F2). The inherent semi-circular structure of the femur makes it vulnerable to robust surface detection by conventional techniques like skeleton reference or zero-crossing. To overcome this, a section separation technique is employed, which ensures the ROI in each section can be individually made robust to zero-crossing-based surface detection. As depicted in FIG. 8, this is done by first finding the bounding box 264 for the total volume and then splitting the image (within the bounding box 264) into three sections: left half 266, upper right half 268, and lower right half 270.

For the surface separation stage for the femoral cartilage region, the method 244 further includes performing articular surface extraction via two-dimensional (2D) zero-crossing on each section 260 (block 272, step F3). Once the volume is split into left half 266, upper right half 268, and lower right half 270, 2D zero-crossing is performed in each image (section) in directions 274 as shown in FIG. 8 and the first non-zero pixel is extracted to form the articular surface.

For the surface separation stage for the femoral cartilage region, the method 244 further includes aggregating articular surfaces extracted from each section 260 to generate an articular surface (e.g., articular surface volume) 276 of an entirety of the femoral cartilage volume (block 278, step F4). In particular, the articular surfaces extracted from each section 260 are stitched together to get the articular surface 276 of the entire femoral cartilage volume.

For the surface separation stage for each of the tibial cartilage region, the patellar cartilage region, and the meniscal cartilage region, the method 244 includes detecting boundaries of an inputted non-femoral cartilage region 280 (e.g., pre-processed non-femoral cartilage ROI volume) utilizing distance transform to generate respective contour images and performing three-dimensional (3D) connected component analysis on the respective contour images to generate a respective plurality 282 of contour images (for each connected component) for each non-femoral cartilage region (block 284, step a1). For the patellar cartilage region, and the meniscal cartilage region, each connected component is treated as a separate volume for the subsequent stages of the algorithm (e.g., steps a2-a4). This is needed, since the surface separation techniques used by the algorithm rely on having a single ROI voxel in at least one direction of the image.

Figure 9:
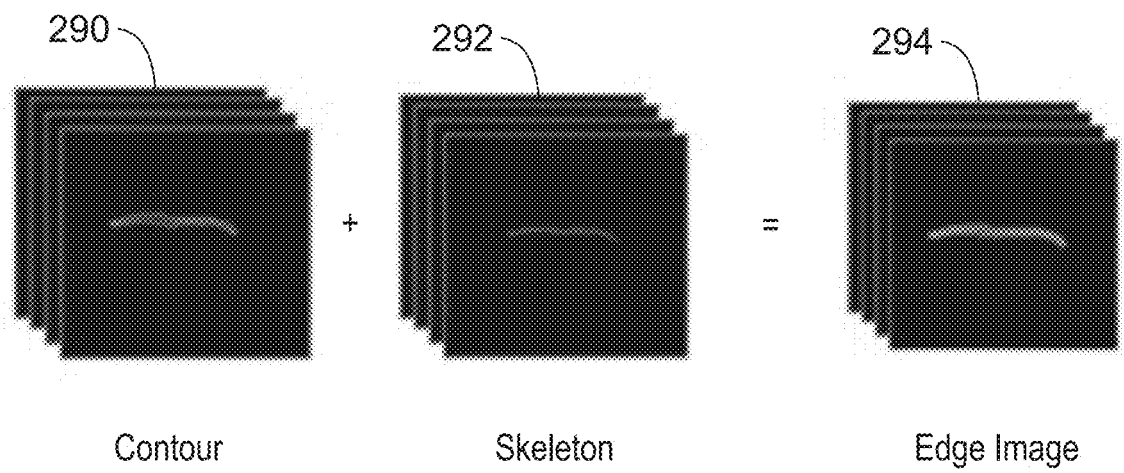
FIG. 9 illustrates contour detection, skeletonization edge image creation for a tibial cartilage region of interest, in accordance with aspects of the present disclosure.

For the surface separation stage for each of the tibial cartilage region, the patellar cartilage region, and the meniscal cartilage region, the method 244 also includes performing skeletonization on the respective plurality 282 of contour images to generate respective edge images 286 for each of the tibial cartilage region, the patellar cartilage region, and the meniscal cartilage region (block 288, step a2). For cartilages other than femoral cartilage, contour detection and connected component analysis is followed by skeletonization. As depicted in FIG. 9, skeletonization reduces binary images 290 (of the plurality 282 of contour images) to 1-pixel wide representations 292 (skeleton images). This technique is generally used for feature extraction, and/or representing an image's topology. Here, it is used a means to extract articular surface, where the distance transform images 290 and skeleton images 292 are added to create an edge image 294. FIG. 9 demonstrates this process for the tibial cartilage region.

For the surface separation stage for each of the tibial cartilage region, the patellar cartilage region, and the meniscal cartilage region, the method 244 further includes performing articular surface extraction utilizing the union method or technique to obtain extracted articular surface volumes 296 for each connected component (block 298). The first step in the union method is articular surface extraction through the skeleton reference method. The skeleton reference method for each of the tibial and meniscal cartilage regions includes spanning the whole edge image (e.g. edge image 294 in FIG. 9) and extracting all the pixels that lie above the skeleton-articular surface. The skeleton reference method for the patellar cartilage region includes spanning the whole edge image (e.g., edge image 294 in FIG. 9) and extracting all the pixels which lie to right of the skeleton-articular surface.

For cartilages other than femoral cartilage, contour detected volumes (e.g., distance transform images in FIG. 9) are also subjected to zero-crossing-based surface detection in 2D as follows. Zero-crossing-based surface detection for each of the tibial and meniscal cartilage regions includes spanning the entire image (e.g., contour detected volume 290 in FIG. 9) from top (superior) to bottom (inferior) or vice versa and extracting the first non-zero pixel at the articular surface interface. Zero-crossing-based surface detection for the patellar region includes spanning the entire image (e.g., contour detected volume 290 in FIG. 9) from right (anterior) to left (posterior) or vice versa and extracting the first non-zero pixel at the articular or subchondral surface interface. When scanning from right to left, the first non-zero pixel encountered will be from the articular surface. When scanning from left to right, the first non-zero pixel encountered will be from the subchondral surface.

The final articular surface for tibial cartilage, patellar cartilage, and meniscal cartilage is computed as the union of articular surfaces generated via skeleton reference as well as zero crossing methods. The challenge with skeleton reference is that the detected skeleton sometimes misses the endpoints of the ROIs by a few pixels, which results in the extracted surfaces appearing smaller than the original surfaces. The zero-crossing method suffers from a challenge due to spanning direction, in that a significant vertical step change in case of tibial cartilage (or a horizontal step change in case of patellar cartilage), might cause the extracted surface to be discontinuous. The union method addresses both these challenges, by combining the best of both, to produce a robust articular surface.

For the surface separation stage for each of the tibial cartilage region, the patellar cartilage region, and the meniscal cartilage region, the method 244 further includes generating (via aggregation) a respective articular surface volume 300 of a respective entirety of a tibial cartilage volume, a patellar cartilage volume, and a meniscal cartilage volume based on the respective extracted pixels and the respective first non-zero pixels obtained in block 298 (block 302). In particular, the articular surfaces extracted via the union method from all of the connected components (separated in step a1) are aggregated to obtain the articular surface volume for the respective cartilage region.

The method 244 also includes performing surface separation for each of the femoral cartilage region, the tibial cartilage region, the patellar cartilage region, and the meniscal cartilage region performing bone surface extraction by subtracting the respective articular surface from the respective contour image to generate a respective bone surface volume 304 (block 306, step $B_1$). The method 244 further includes for each of the femoral cartilage region, the tibial cartilage region, the patellar cartilage region, and the meniscal cartilage region performing post-processing for refinement of the generated surfaces (i.e., the respective articular surfaces and the respective bone (subchondral) surfaces) to generate post-processed bone (subchondral) surface volumes 308 and articular surface volumes (block 310). Refinement operations improve the robustness of surface separation. Refinement operations include detecting ROI voxels with single pixel thickness and adding them back to the originally extracted subchondral surface. Refinement operations also include detecting and removing any discontinuous or unconnected voxels with sizes less than a predefined threshold in the subchondral surface.

Figure 10:
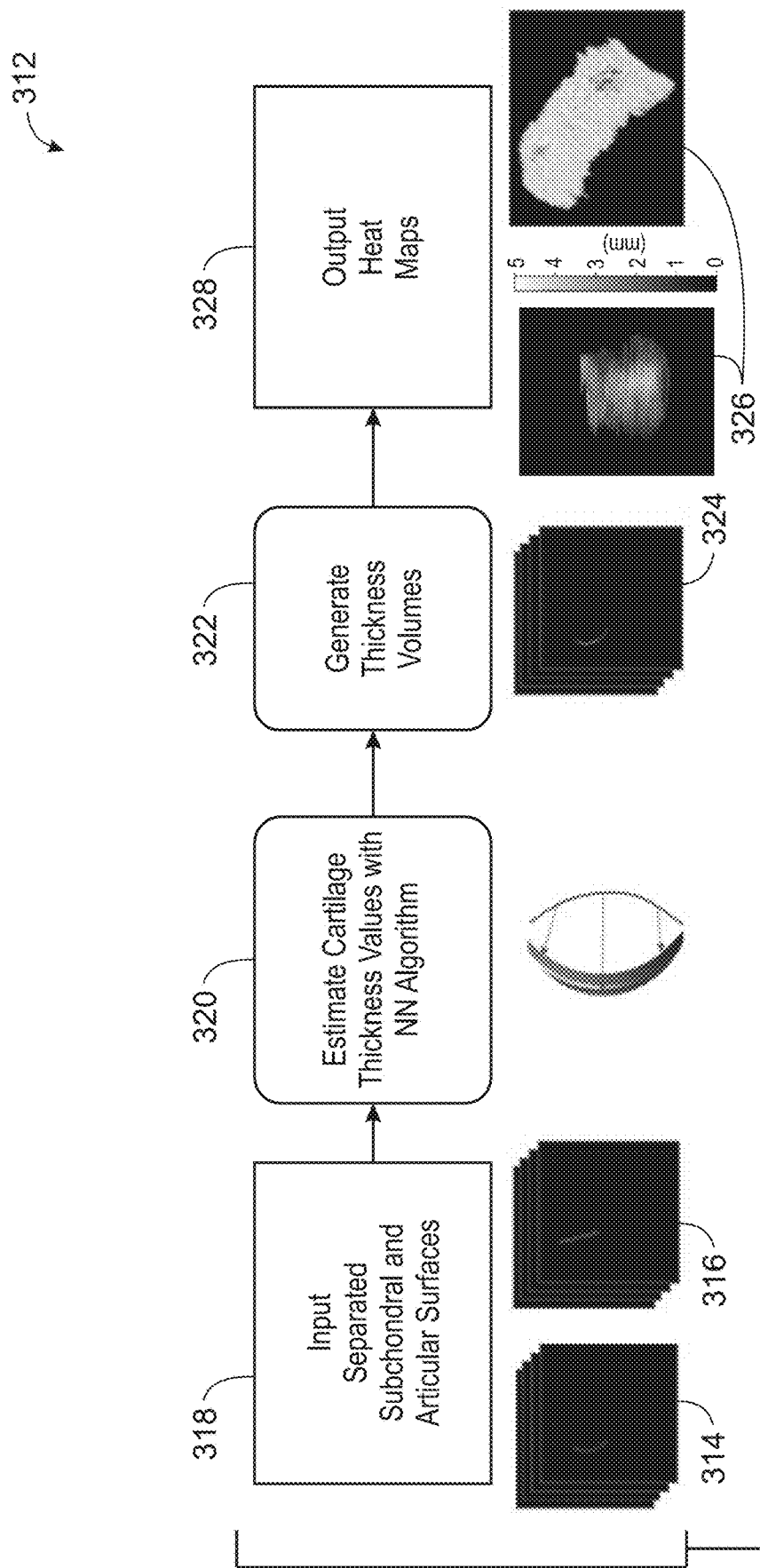
FIG. 10 illustrates a schematic diagram of a method for a thickness computation stage of a thickness estimation algorithm, in accordance with aspects of the present disclosure.

FIG. 10 illustrates a schematic diagram of a method 312 for a thickness computation stage of the thickness estimation algorithm 195 in FIG. 3. One or more steps of the method 312 may be performed by processing circuitry of the magnetic resonance imaging system 100 in FIG. 1 or a remote computing system. The method 312 may be utilized on multiple slices of MRI image data.

The method 312 includes (for each of the femoral cartilage region, the tibial cartilage region, the patellar cartilage region, and the meniscal cartilage region) inputting into the algorithm 195 the separated subchondral surface 314 and articular surface (block 318). The method 312 also includes estimating respective cartilage thickness values for each of femoral cartilage, tibial cartilage, patellar cartilage, and meniscal cartilage utilizing a nearest neighbor algorithm based on the respective separate subchondral surfaces and the respective separate articular surfaces (block 320). For each slice, the corresponding subchondral/bone surfaces are chosen as the reference 2D surface, while 3D point cloud includes the entire articular/cartilage surface volume in each case. For each point on the bone surface, the Euclidean distance to each point on the cartilage surface is calculated. The cartilage thickness assigned to the bone surface point is the minimum of those distances. In certain embodiments, the articular/cartilage surface is utilized as the reference 2D surface and the subchondral/bone surface volume is utilized as the 3D point cloud.

The method 312 further includes generating a respective thickness volume 324 for each of the femoral cartilage, the tibial cartilage, the patellar cartilage, and the meniscal cartilage with the respective cartilage thickness values encoded to pixels of either the respective separate subchondral surface or the respective separate articular surface (block 322) The thickness values are encoded to the pixels of the subchondral surface or the articular surface and converted to DICOM files (DICOM volumes 316) to facilitate 3D visualization in DICOM viewer applications. The method 312 even further includes outputting a respective heat map 326 (e.g., 2D heat map or 3D heat map) for each of the femoral cartilage, the tibial cartilage, the patellar cartilage, and the meniscal cartilage based on the respective thickness volume 324 for visualization on a display (block 328).

FIGS. 11-22 illustrate the multi-fold validation performed to determine the accuracy and efficacy of the algorithm (algorithm 195 in FIG. 3). The algorithm was tested on artificially created digital phantoms with structural similarities to the ROIs (e.g., the femoral cartilage region, the tibial cartilage region, the patellar cartilage region, and the meniscal cartilage region) and having pre-defined thickness values. Digital phantoms were created for the femoral cartilage, tibial cartilage, and the patellar cartilage. Utilizing the digital phantom, it was found that the algorithm estimates thickness values accurately.

Figure 11:
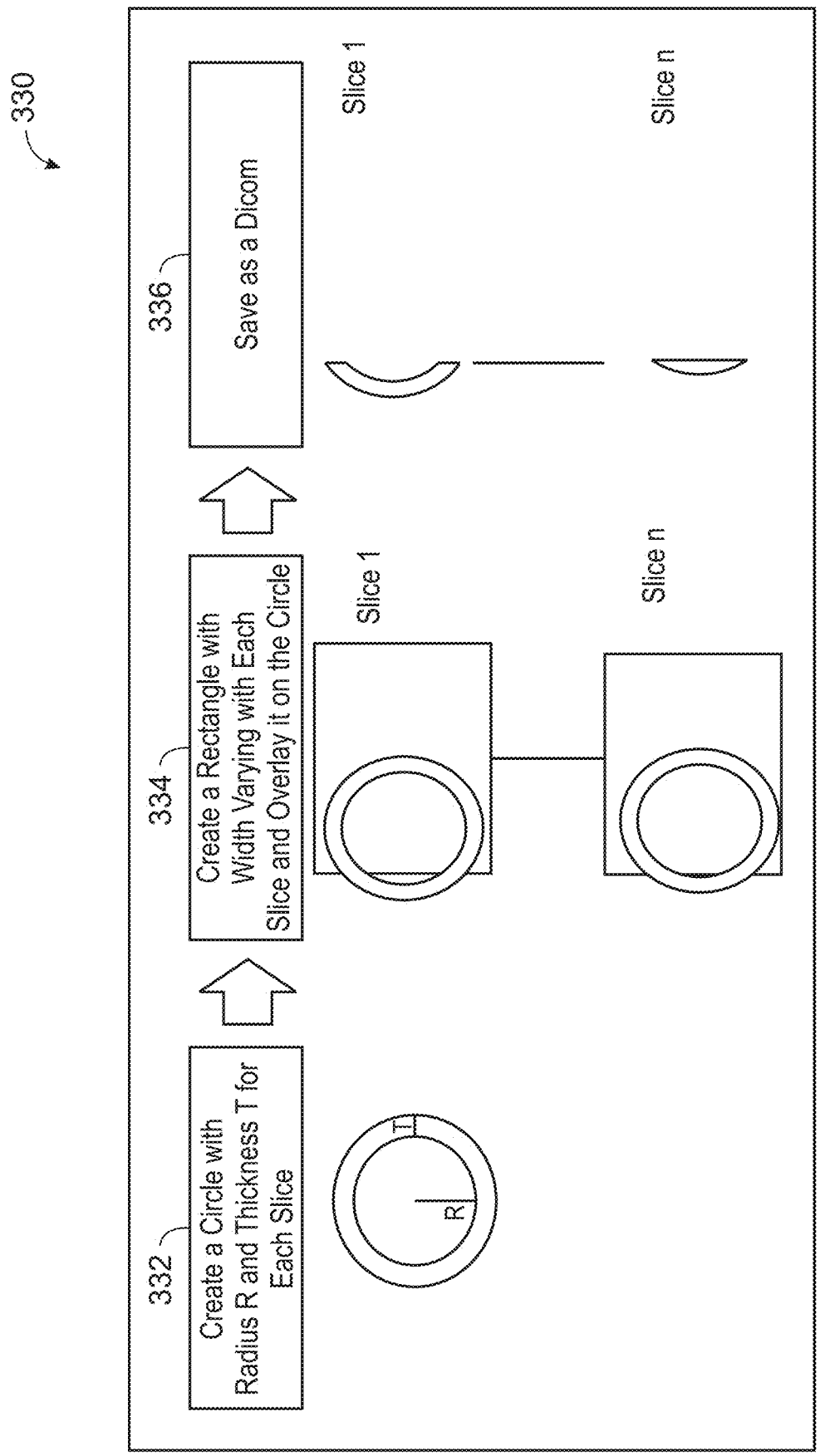
FIG. 11 illustrates a schematic diagram of a method for creating a digital phantom for patellar cartilage, in accordance with aspects of the present disclosure.

FIG. 11 illustrates a schematic diagram of a method 330 for creating a digital phantom for patellar cartilage (which applies to the other types of cartilages). One or more steps of the method 330 may be performed by processing circuitry of the magnetic resonance imaging system 100 in FIG. 1 or a remote computing system.

Figure 12:
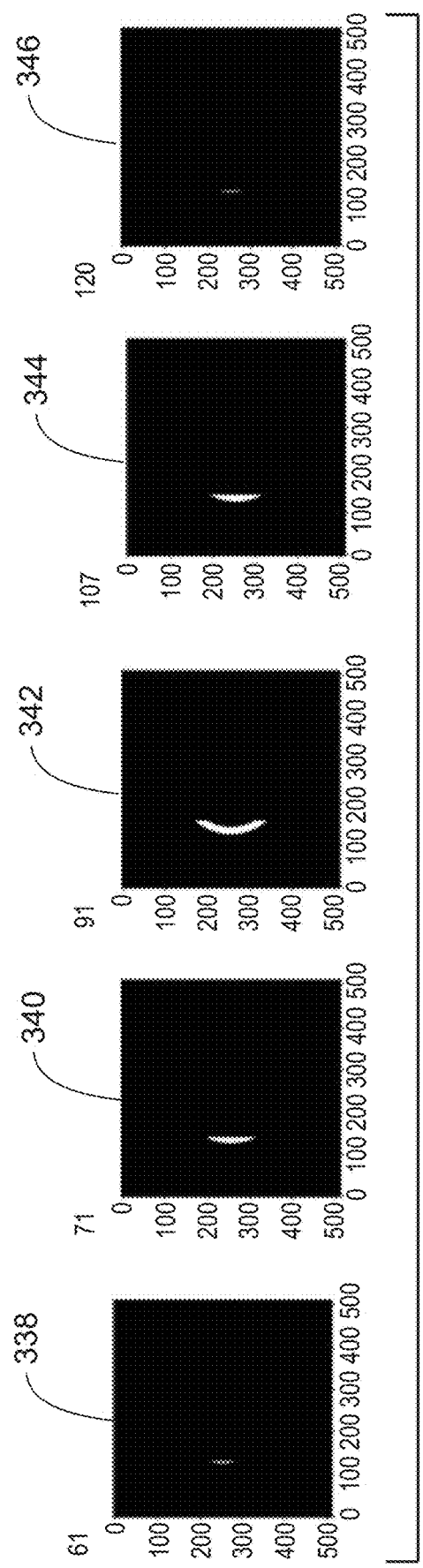
FIG. 12 depicts different slice volumes of a digital phantom for patellar cartilage generated utilizing the method in FIG. 11, in accordance with aspects of the present disclosure.

The method 330 includes creating a circle with a radius (R) (e.g., R=120 pixels) and a thickness (T) (e.g., T=15 pixels) (block 332). The method 330 also includes creating a rectangle with a width varying with each slice and overlaying it on the circle (block 334). The method 330 further includes generating in each slice a shape of the resultant image saving it as a DICOM file (block 336). FIG. 12 depicts different slice volumes (e.g., slice volumes 338, 340, 342, 344, and 346) of a digital phantom for patellar cartilage generated utilizing the method 330 in FIG. 11.

Figure 13:
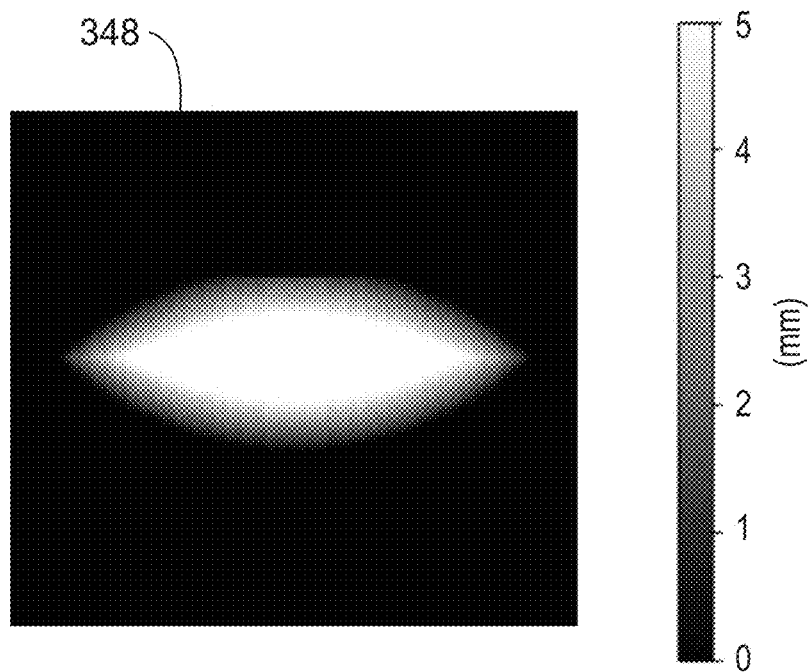
FIGS. 13 and 14 depict different thickness maps (heat maps) generated from a couple of digital phantoms for patellar cartilage, in accordance with aspects of the present disclosure.
Figure 14:
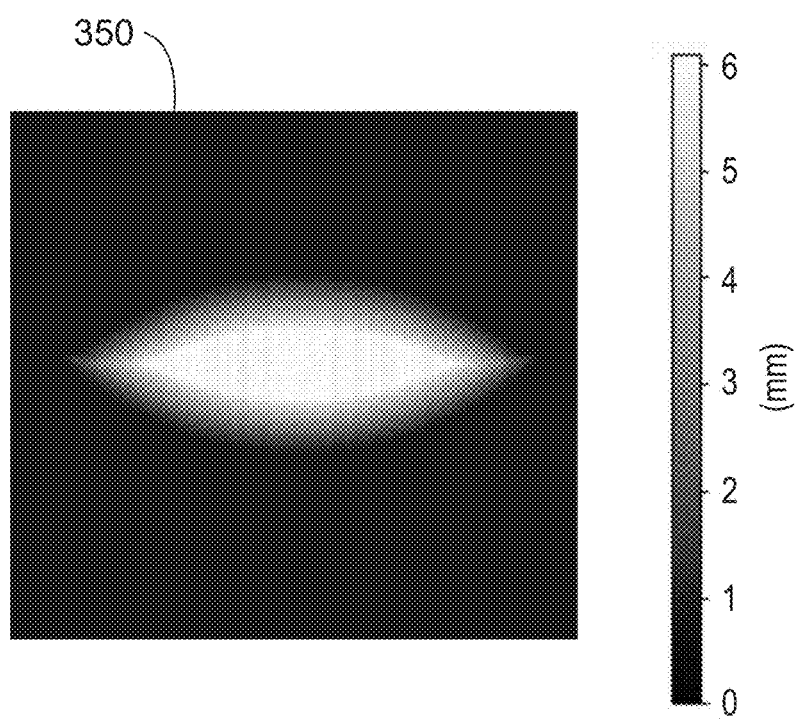

FIGS. 13 and 14 depict different thickness maps (heat maps) 348 and 350 generated from a couple of digital phantoms for patellar cartilage. The algorithm 195 (e.g., thickness estimation algorithm) in FIG. 3 was executed on a couple different phantoms with different thicknesses.

Figure 15:
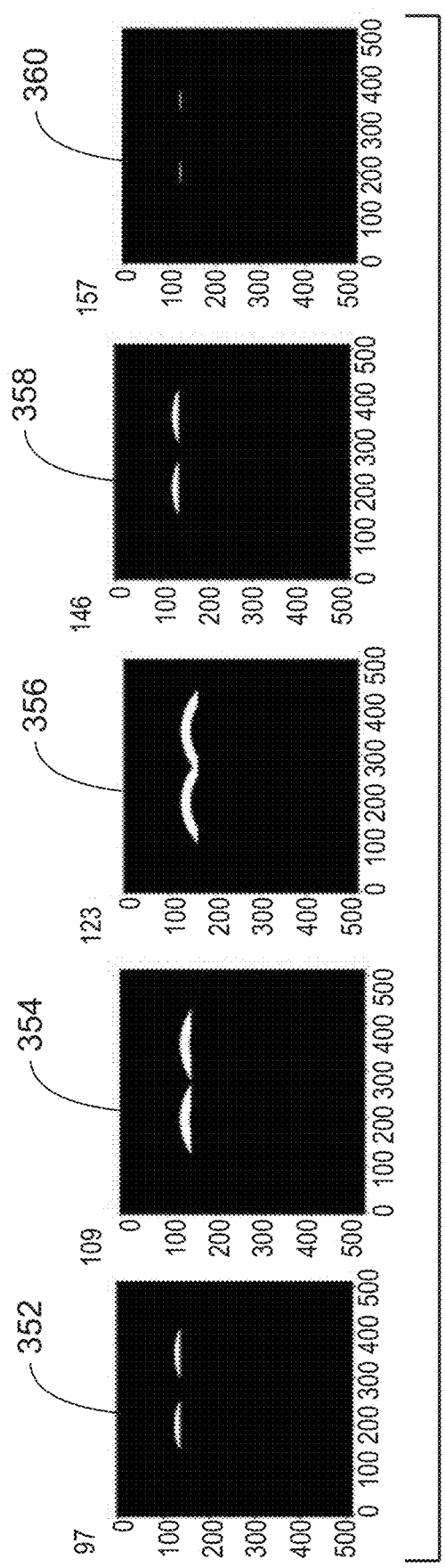
FIG. 15 depicts different slice volumes of a digital phantom for tibial cartilage, in accordance with aspects of the present disclosure.
Figure 16:
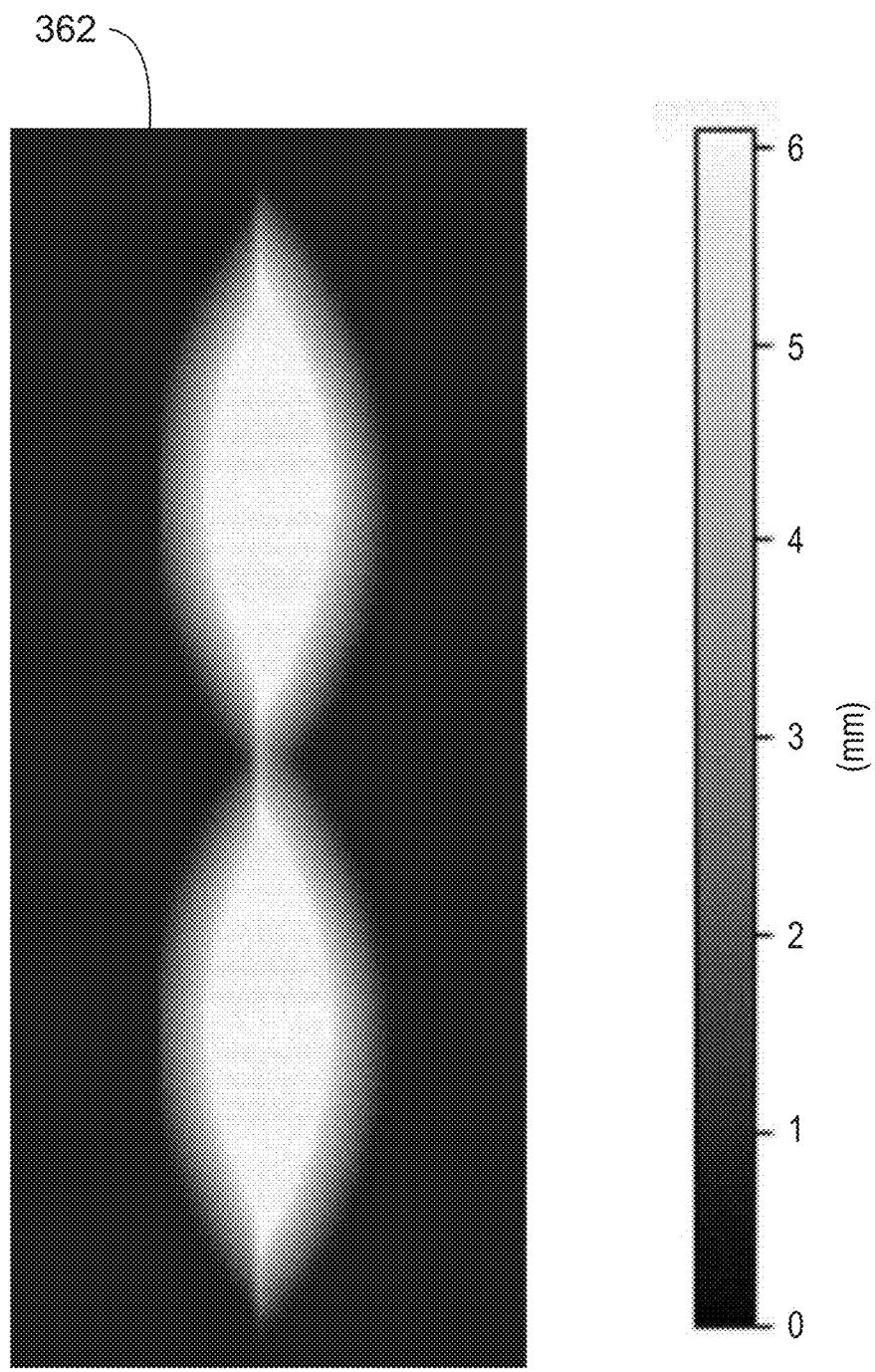
FIG. 16 depicts a thickness map (heat map) generated from a digital phantom for tibial cartilage, in accordance with aspects of the present disclosure.

FIG. 15 depicts different slice volumes (e.g., slice volumes 352, 354, 356, 358, and 360) of a digital phantom for tibial cartilage generated utilizing the method 330 in FIG. 11. FIG. 16 depicts a thickness map (heat map) 362 generated from a slice of a digital phantom for tibial cartilage.

Figure 17:
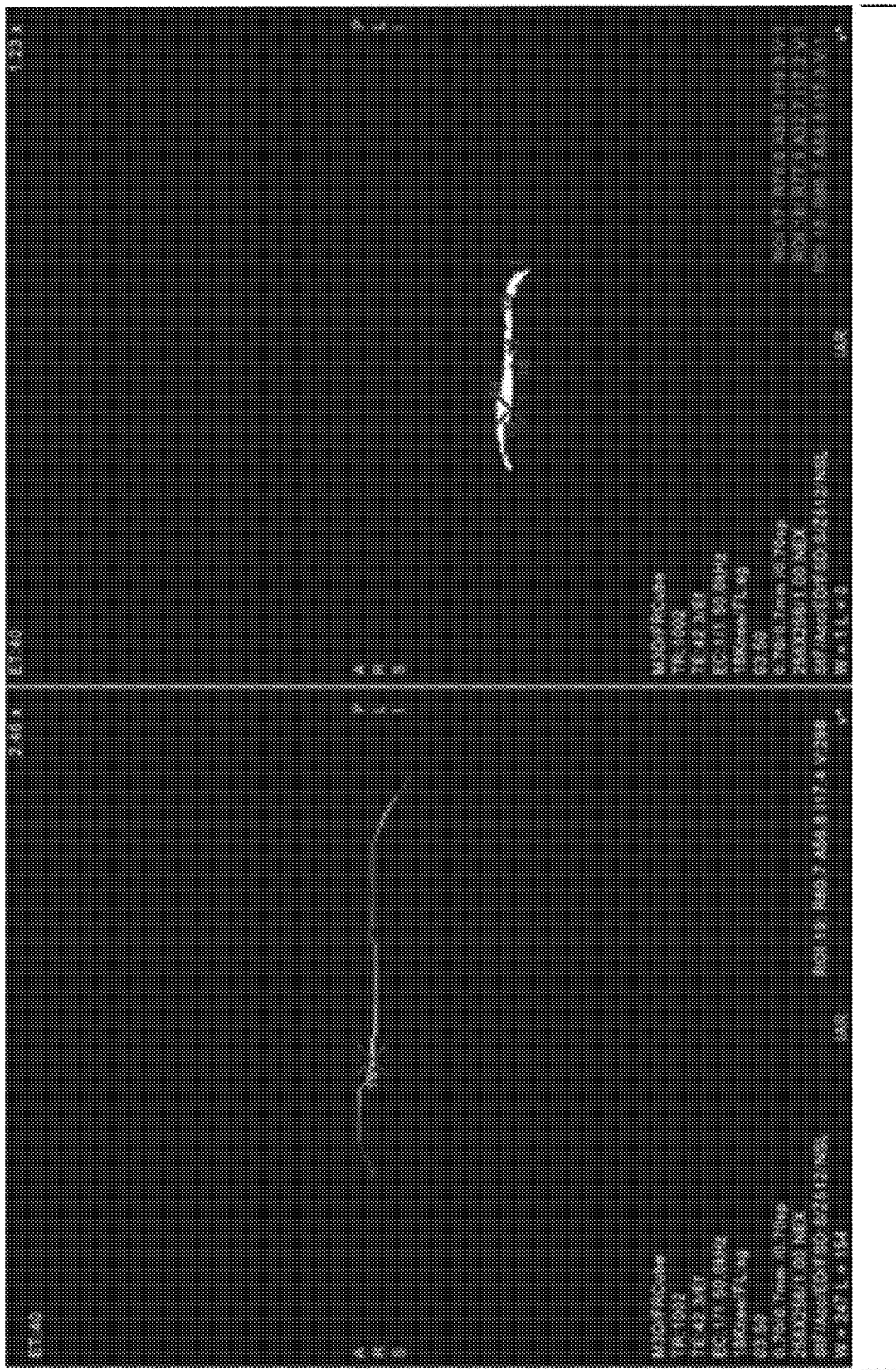
FIG. 17 depicts a process for manual validation of tibial cartilage thickness.
Figure 18:
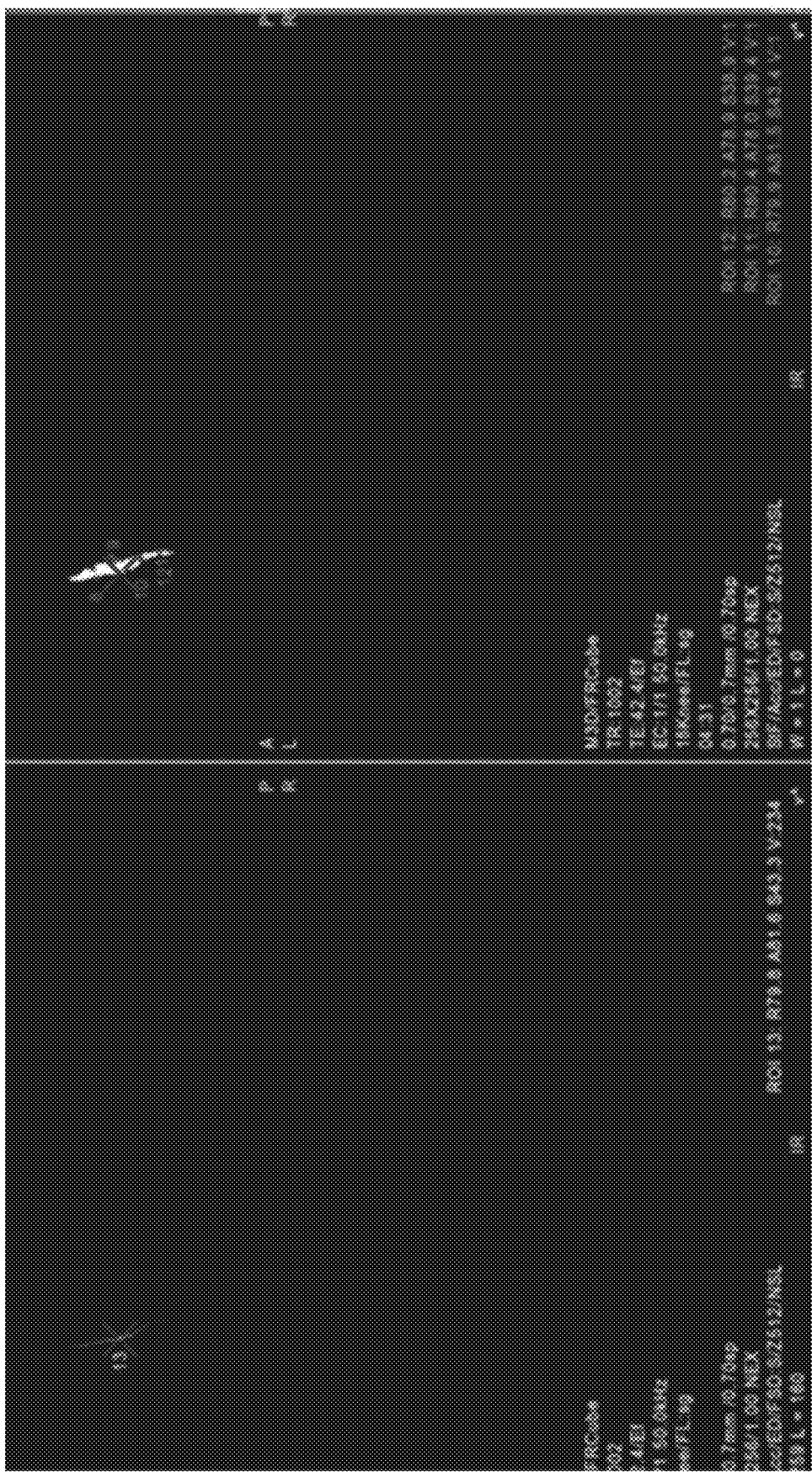
FIG. 18 depicts a process for manual validation of patellar cartilage thickness.
Figure 19:
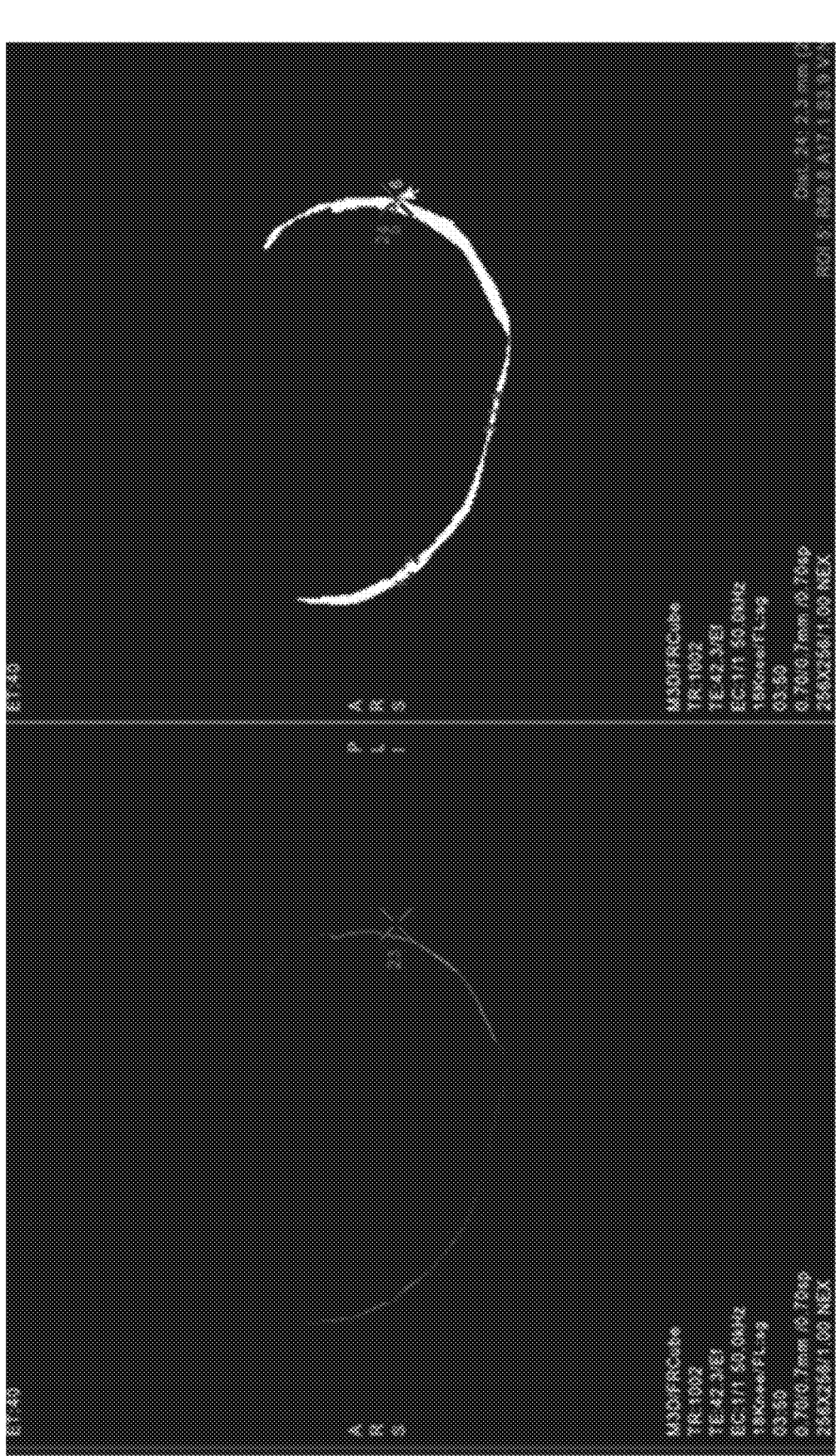
FIG. 19 depicts a process for manual validation of femoral cartilage thickness.

Segmented ROIs from 15 knee scan volumes acquired via an MRI scanner utilizing a sagittal isotropic 3D fast (turbo) spin echo sequence optimized for half Fourier parallel imaging, with long echo trains, low flip angles, and low specific absorption rates were also subjected to manual thickness computation by clinical experts as a means of further validation. In particular, clinical experts picked pairs of key points from both surfaces of the segmented ROI and computed thickness between them by means of available measurement tools. FIGS. 17-19 are snapshots utilizing Volume Viewer (e.g., from GE Healthcare) depicting the process. FIG. 17 depicts the process for tibial cartilage thickness validation. FIG. 18 depicts the process for patellar cartilage validation. FIG. 19 depicts the process for femoral cartilage validation. The left side of each of FIGS. 17-19 are the DICOM volumes encoded with thickness valued along a surface. The right side of each of FIGS. 17-19 shows the actual labeling with key points chosen by clinical experts.

The chosen key point pairs by clinical experts are saved and compared with the thickness values estimated by the algorithm. For each dataset, at least 3 pairs of points were chosen for manual validation. The method was done on femoral cartilage, tibial cartilage, and patellar cartilage. The validation of the meniscal cartilage was only performed visually and was found to be generally acceptable. The results from the manual validation tabulated for the 3 pairs of points are depicted in FIGS. 20-22. FIG. 20 depicts tables 364, 366, 368 of results of manual validation of femoral cartilage thickness. Each table 364, 366, 368 represents a different pair of points between the thicknesses measured by the clinical experts and the thicknesses measured by the algorithm. FIG. 21 depicts tables 370, 372, 374 of results of manual validation of tibial cartilage thickness. Each table 370, 372, 374 represents a different pair of points between the thicknesses measured by the clinical experts and the thicknesses measured by the algorithm. FIG. 22 depicts tables 376, 378, 380 of results of manual validation of patellar cartilage thickness. Each table 376, 378, 380 represents a different pair of points between the thicknesses measured by the clinical experts and the thicknesses measured by the algorithm. In each of the FIGS. 20-22, the maximum error has been circled. The minimum error value out of all computations was 0.059 millimeters (mm) and the maximum error was 1.2 mm. Most of the error values were found to lie within the acceptable range of 0.5 mm, thus, demonstrating the efficacy of the disclosed algorithm.

Technical effects of the disclosed subject matter include an easy, generic and less computationally intensive algorithm that can be used to estimate the thickness of all 4 cartilages (femoral, tibial, patellar, and meniscal) which can be visualized in 2D or 3D. Additional technical effects include enabling accurate analysis of cartilage thickness values over time to help in assessing progression of cartilage degeneration (if any) and early treatment. Further, technical effects include providing an automated technique for estimating cartilage thickness that avoids the drawbacks of other techniques while also enabling a faster diagnosis. Further, the technical effects include reducing computing and/or processing requirements on the system and delivering faster throughput by not utilizing deep learning techniques in estimating the cartilage thickness values. Even further, the technical effects include providing a standardized way computing the estimates that ensure high repeatability and improved measurement accuracy over time. Still further, as the estimated cartilage thickness values are quantitative, the technical effects include providing a better assessment of progression of degeneration over time. Yet further, the technical effects include providing for different techniques for the user to visualize and report the findings from thickness maps which may further aid in diagnosis and treatment.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A computer-implemented method for estimating cartilage thickness, comprising:
 pre-processing, via a processor, a segmented image of region of interests (ROIs) of a subject to separate the

ROIs into individual ROI volumes, wherein the ROI volumes comprise at least one cartilage region;

performing, via the processor, surface separation between a respective subchondral surface and a respective articular surface for each ROI volume to extract a respective separate subchondral surface and a respective separate articular surface for each ROI volume; and estimating, via the processor, cartilage statistics for the at least one cartilage region utilizing a nearest neighbor algorithm based on the respective separate subchondral surface and the respective separate articular surface for each ROI volume.

2. The computer-implemented method of claim 1, wherein the ROI volumes comprise a femoral cartilage region, a tibial cartilage region, a patellar cartilage region, and a meniscal cartilage region, and wherein estimating cartilage statistics for the at least one cartilage region comprises estimating respective cartilage thickness values for each of femoral cartilage, tibial cartilage, patellar cartilage, and meniscal cartilage.

3. The computer-implemented method of claim 2, further comprising:

generating, via the processor, a respective thickness volume for each of the femoral cartilage, the tibial cartilage, the patellar cartilage, and the meniscal cartilage with the respective cartilage thickness values encoded to pixels of either the respective separate subchondral surface or the respective separate articular surface; and outputting, via the processor, a respective heat map for each of the femoral cartilage, the tibial cartilage, the patellar cartilage, and the meniscal cartilage based on the respective thickness volume for visualization on a display.

4. The computer-implemented method of claim 2, wherein pre-processing comprises:

performing, via the processor, thresholding and binarization to extract the ROI volumes from the segmented image; and removing, via the processor, stray pixels from the ROI volumes.

5. The computer-implemented method of claim 2, wherein estimating the respective cartilage thickness values comprises utilizing one of the respective separate subchondral surface and the respective separate articular surface as a reference two-dimensional surface while utilizing the other of the respective separate subchondral surface and the respective separate articular surface as a three-dimensional point cloud for each of the femoral cartilage, the tibial cartilage, the patellar cartilage, and the meniscal cartilage when utilizing the nearest neighbor algorithm.

6. The computer-implemented method of claim 2, wherein performing surface separation for the femoral cartilage region comprises:

detecting, via the processor, boundaries of the femoral cartilage region utilizing distance transform to generate a contour image;

designating, via the processor, a bounding box for a total volume in the contour image;

separating, via the processor, the bounding box into multiple sections;

performing, via the processor, articular surface extraction via two-dimensional zero-crossing on each section of the multiple sections; and aggregating, via the processor, articular surfaces extracted from each section of the multiple sections to generate an articular surface of an entirety of a femoral cartilage volume.

7. The computer-implemented method of claim 6, wherein performing surface separation for the femoral cartilage region comprises:

subtracting, via the processor, the articular surface from the contour image to generate a bone surface; and refining, via the processor, each of the articular surface and the bone surface.

8. The computer-implemented method of claim 2, wherein performing surface separation for each of the tibial cartilage region, the patellar cartilage region, and the meniscal cartilage region comprises:

detecting, via the processor, respective boundaries of the tibial cartilage region, the patellar cartilage region, and the meniscal cartilage region utilizing distance transform to generate respective contour images;

performing, via the processor, three-dimensional (3D) connected component analysis on the respective contour images to generate a respective plurality of contour images for each of the tibial cartilage region, the patellar cartilage region, and the meniscal cartilage region;

performing, via the processor, skeletonization on the respective plurality of contour images to generate respective edge images for each of the tibial cartilage region, the patellar cartilage region, and the meniscal cartilage region by adding the respective plurality of contour images to skeleton images for the each of the tibial cartilage region, the patellar cartilage region, and the meniscal cartilage region;

for the respective edge images of both the tibial cartilage region and the meniscal cartilage region, while spanning an entirety of each respective edge image, extracting, via the processor, all pixels above a skeleton-articular surface interface;

for the respective edge images of the patellar cartilage region, while spanning an entirety of each respective edge image, extracting, via the processor, all pixels lie to right of skeleton-articular surface interface;

for the respective plurality of contour images of both the tibial cartilage region and the meniscal cartilage region, while spanning an entirety of each respective contour image from superior to inferior, performing, via the processor, articular surface extraction via two-dimensional zero-crossing to extract a respective non-zero pixel at an articular surface interface;

for the respective plurality of contour images of the patellar cartilage region, while spanning an entirety of each respective contour image from anterior to posterior, performing, via the processor, articular surface extraction via two-dimensional zero-crossing to extract a respective non-zero pixel at the articular surface interface; and generating, via the processor, a respective articular surface of a respective entirety of a tibial cartilage volume, a patellar cartilage volume, and a meniscal cartilage volume based on the union of respective extracted pixels and the respective first non-zero pixels.

9. The computer-implemented method of claim 8, wherein performing surface separation for each of the tibial cartilage region, the patellar cartilage region, and the meniscal cartilage region comprises:

subtracting, via the processor, the respective articular surface from the respective contour image to generate a respective bone surface; and refining, via the processor, each of the respective articular surface and the respective bone surface.

10. A system for estimating knee cartilage thickness, comprising:
a memory encoding processor-executable routines; and
a processor configured to access the memory and to execute the processor-executable routines, wherein the routines, when executed by the processor, cause the processor to:
pre-process a segmented image of region of interests (ROIs) of a knee of a subject to separate the ROIs into individual ROI volumes, wherein the ROI volumes comprise at least one cartilage region;
perform surface separation between a respective subchondral surface and a respective articular surface for each ROI volume to extract a respective separate subchondral surface and a respective separate articular surface for each ROI volume; and
estimate cartilage thickness values for the at least one cartilage region utilizing a nearest neighbor algorithm based on the respective separate subchondral surface and the respective separate articular surface for each ROI volume.

11. The system of claim 10, wherein the ROI volumes comprise a femoral cartilage region, a tibial cartilage region, a patellar cartilage region, and a meniscal cartilage region, and wherein estimating cartilage thickness values for the at least one cartilage region comprises estimating respective cartilage thickness values for each of femoral cartilage, tibial cartilage, patellar cartilage, and meniscal cartilage.

12. The system of claim 11, wherein the routines, when executed by the processor, cause the processor to:
generate a respective thickness volume for each of the femoral cartilage, the tibial cartilage, the patellar cartilage, and the meniscal cartilage with the respective cartilage thickness values encoded to pixels of either the respective separate subchondral surface or the respective separate articular surface; and
output a respective heat map for each of the femoral cartilage, the tibial cartilage, the patellar cartilage, and the meniscal cartilage based on the respective thickness volume for visualization on a display.

13. The system of claim 11, wherein pre-processing comprises:
performing thresholding and binarization to extract the ROI volumes from the 5-class segmented image; and
removing stray pixels from the ROI volumes.

14. The system of claim 11, wherein estimating the respective cartilage thickness values comprises utilizing one of the respective separate subchondral surface and the respective separate articular surface as a reference two-dimensional surface while utilizing the other of the respective separate subchondral surface and the respective separate articular surface as a three-dimensional point cloud for each of the femoral cartilage, the tibial cartilage, the patellar cartilage, and the meniscal cartilage when utilizing the nearest neighbor algorithm.

15. The system of claim 11, wherein performing surface separation for the femoral cartilage region comprises:
detecting boundaries of the femoral cartilage region utilizing distance transform to generate a contour image;
designating a bounding box for a total volume in the contour image;
separating the bounding box into multiple sections;
performing articular surface extraction via two-dimensional zero-crossing on each section of the multiple sections; and
aggregating articular surfaces extracted from each section of the multiple sections to generate an articular surface of an entirety of a femoral cartilage volume.

16. The system of claim 15, wherein performing surface separation for the femoral cartilage region comprises:
subtracting the articular surface from the contour image to generate a bone surface; and
refining each of the articular surface and the bone surface.

17. The system of claim 11, wherein performing surface separation for each of the tibial cartilage region, the patellar cartilage region, and the meniscal cartilage region comprises:
detecting respective boundaries of the tibial cartilage region, the patellar cartilage region, and the meniscal cartilage region utilizing distance transform to generate respective contour images;
performing three-dimensional (3D) connected component analysis on the respective contour images to generate a respective plurality of contour images for each of the tibial cartilage region, the patellar cartilage region, and the meniscal cartilage region;
performing skeletonization on the respective plurality of contour images to generate respective edge images for each of the tibial cartilage region, the patellar cartilage region, and the meniscal cartilage region by adding the respective plurality of contour images to skeleton images for the each of the tibial cartilage region, the patellar cartilage region, and the meniscal cartilage region;
for the respective edge images of both the tibial cartilage region and the meniscal cartilage region, while spanning an entirety of each respective edge image, extracting all pixels above a skeleton-articular surface interface;
for the respective edge images of the patellar cartilage region, while spanning an entirety of each respective edge image, extracting all pixels lie to right of skeleton-articular surface interface;
for the respective plurality of contour images of both the tibial cartilage region and the meniscal cartilage region, while spanning an entirety of each respective contour image from superior to inferior, performing articular surface extraction via two-dimensional zero-crossing to extract a respective non-zero pixel at an articular surface interface;
for the respective plurality of contour images of the patellar cartilage region, while spanning an entirety of each respective contour image from anterior to posterior, performing articular surface extraction via two-dimensional zero-crossing to extract a respective non-zero pixel at the articular surface interface; and
generating a respective articular surface of a respective entirety of a tibial cartilage volume, a patellar cartilage volume, and a meniscal cartilage volume based on the union of respective extracted pixels and the respective first non-zero pixels.

18. The system of claim 17, wherein performing surface separation for each of the tibial cartilage region, the patellar cartilage region, and the meniscal cartilage region comprises:
subtracting the respective articular surface from the respective contour image to generate a respective bone surface; and refining each of the respective articular surface and the respective bone surface.

19. A non-transitory computer-readable medium, the computer-readable medium comprising processor-executable code that when executed by a processor, causes the processor to:
pre-process a segmented image of region of interests (ROIs) of a knee of a subject to separate the ROIs into individual ROI volumes, wherein the ROI volumes comprise at least one cartilage region;
perform surface separation between a respective subchondral surface and a respective articular surface for each ROI volume to extract a respective separate subchondral surface and a respective separate articular surface for each ROI volume; and
estimate cartilage thickness values for the at least one cartilage region utilizing a nearest neighbor algorithm based on the respective separate subchondral surface and the respective separate articular surface for each ROI volume, wherein pre-processing the segmented image, performing surface separation, and estimating cartilage thickness values all occur without utilizing deep-learning.

20. The non-transitory computer-readable medium of claim 19, wherein the ROI volumes comprise a femoral cartilage region, a tibial cartilage region, a patellar cartilage region, and a meniscal cartilage region, and wherein estimating cartilage thickness values for the at least one cartilage region comprises estimating respective cartilage thickness values for each of femoral cartilage, tibial cartilage, patellar cartilage, and meniscal cartilage, and wherein the code, when executed by the processor, cause the processor to:
generate a respective thickness volume for each of the femoral cartilage, the tibial cartilage, the patellar cartilage, and the meniscal cartilage with the respective cartilage thickness values encoded to pixels of either the respective separate subchondral surface or the respective separate articular surface; and
output a respective two-dimensional or three dimensional color map or surface/volume rendering for each of the femoral cartilage, the tibial cartilage, the patellar cartilage, and the meniscal cartilage based on the respective thickness volume for visualization on a display.

21. The non-transitory computer-readable medium of claim 20, wherein the processor-executable code when executed by a processor, causes the processor to export or save the respective two-dimensional or three dimensional color map or surface/volume rendering for each of the femoral cartilage, the tibial cartilage, the patellar cartilage, and the meniscal cartilage in a three-dimensional printer compatible format.

* * * * *